United States Patent [19]
Komiya et al.

[11] Patent Number: 5,872,275
[45] Date of Patent: Feb. 16, 1999

[54] PROCESS FOR THE PRODUCING OF AROMATIC CARBONATE

[75] Inventors: Kyosuke Komiya; Masahiro Tojo; Shinsuke Fukuoka, all of Kurashiki, Japan

[73] Assignee: Asahi Kasei Kogyo Kabushiki Kaisha, Osaka, Japan

[21] Appl. No.: 913,883

[22] PCT Filed: Sep. 20, 1996

[86] PCT No.: PCT/JP96/02734

§ 371 Date: Sep. 24, 1997

§ 102(e) Date: Sep. 24, 1997

[87] PCT Pub. No.: WO97/11049

PCT Pub. Date: Mar. 27, 1997

[30] Foreign Application Priority Data

Sep. 22, 1995 [JP] Japan .................................. 7-268036

[51] Int. Cl.$^6$ .................................................. C07C 68/06
[52] U.S. Cl. ........................................... 558/270; 558/274
[58] Field of Search ..................................... 558/270, 274

[56] References Cited

U.S. PATENT DOCUMENTS 5,210,268  5/1993  Fukuoka et al. .
5,380,908  1/1995  Murata et al. .

*Primary Examiner*—Michael G. Ambrose
*Attorney, Agent, or Firm*—Birch, Stewart, Kolasch & Birch, LLP

[57] ABSTRACT

Disclosed is a process for producing an aromatic carbonate which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, wherein the transesterification is conducted while maintaining a weight ratio (WR) of at least one aromatic group-containing substance selected from the group consisting of a specific aromatic polyhydroxy compound and a residue thereof to the metal of the metal-containing catalyst at 2.0 or less, wherein the weight ratio (WR) is measured with respect to a catalyst-containing liquid-phase mixture in a system for the transesterification, and wherein the aromatic group-containing substance originates from the starting material, the reactant and/or a by-product of the transesterification. According to the process of the present invention, the transesterification reaction can be conducted without suffering disadvantageous phenomena, such as the deposition of the catalyst from the catalyst-containing liquid-phase mixture and the adhesion of the deposited catalyst to the inner walls of the reactor, pipes and the like, so that the desired aromatic carbonate can be produced stably for a prolonged period of time.

9 Claims, 3 Drawing Sheets

FIG. 4

PROCESS FOR THE PRODUCING OF AROMATIC CARBONATE

BACKGROUND OF THE INVENTION

1. Field of the Invention

The present invention relates to a process for producing an aromatic carbonate. More particularly, the present invention is concerned with a process for producing an aromatic carbonate which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, wherein the transesterification is conducted while maintaining a weight ratio (WR) of at least one aromatic group-containing substance selected from the group consisting of a specific aromatic polyhydroxy compound and a residue thereof to the metal of the metal-containing catalyst at 2.0 or less, wherein the weight ratio (WR) is measured with respect to a catalyst-containing liquid-phase mixture in a system for the transesterification, and wherein the aromatic group-containing substance originates from the starting material, the reactant and/or a by-product of the transesterification. According to the process of the present invention, the transesterification reaction can be conducted without suffering disadvantageous phenomena, such as the deposition of the catalyst from the catalyst-containing liquid-phase mixture and the adhesion of the deposited catalyst to the inner walls of the reactor, pipes and the like, so that the desired aromatic carbonate can be produced stably for a prolonged period of time.

2. Prior Art

An aromatic carbonate is useful as a raw material for, e.g., the production of an aromatic polycarbonate (whose utility as engineering plastics has been increasing in recent years) without using poisonous phosgene. With respect to the method for the production of an aromatic carbonate, a method for producing an aromatic carbonate or an aromatic carbonate mixture is known, in which a dialkyl carbonate, an alkyl aryl carbonate or a mixture thereof is used as a starting material and an aromatic monohydroxy compound, an alkyl aryl carbonate or a mixture thereof is used as a reactant, and in which a transesterification reaction is performed between the starting material and the reactant.

However, since this type of transesterification is a reversible reaction in which, moreover, not only is the equilibrium biased toward the original system but the reaction rate is also low, the production of an aromatic carbonate by the above-mentioned method on an industrial scale is accompanied with great difficulties.

To improve the above-mentioned method, several proposals have been made, most of which relate to the development of a catalyst for increasing the reaction rate. As a catalyst for use in the method for producing an alkyl aryl carbonate, a diaryl carbonate or a mixture thereof by reacting a dialkyl carbonate with an aromatic hydroxy compound, there have been proposed various metal-containing catalysts, which include for example, a Lewis acid, such as a transition metal halide, or compounds capable of forming a Lewis acid, [see Unexamined Japanese Patent Application Laid-Open Specification No. 51-105032, Unexamined Japanese Patent Application Laid-Open Specification No. 56-123948 and Unexamined Japanese Patent Application Laid-Open Specification No. 56-123949 (corresponding to West German Patent Application Publication No. 2528412, British Patent No. 1499530 and U.S. Pat. No. 4,182,726)], a tin compound, such as an organotin alkoxide or an organotin oxide [Unexamined Japanese Patent Application Laid-Open Specification No. 54-48733 (corresponding to West German Patent Application Publication No. 2736062), Unexamined Japanese Patent Application Laid-Open Specification No. 54-63023, Unexamined Japanese Patent Application Laid-Open Specification No. 60-169444 (corresponding to U.S. Pat. No. 4,554,110), Unexamined Japanese Patent Application Laid-Open Specification No. 60-169445 (corresponding to U.S. Pat. No. 4,552,704), Unexamined Japanese Patent Application Laid-Open Specification No. 62-277345, and Unexamined Japanese Patent Application Laid-Open Specification No. 1-265063], salts and alkoxides of an alkali metal or an alkaline earth metal (Unexamined Japanese Patent Application Laid-Open Specification No. 56-25138), lead compounds (Unexamined Japanese Patent Application Laid-Open Specification No. 57-176932), complexes of a metal, such as copper, iron or zirconium (Unexamined Japanese Patent Application Laid-Open Specification No. 57-183745), titanic acid esters [Unexamined Japanese Patent Application Laid-Open Specification No. 58-185536 (corresponding to U.S. Pat. No. 4,410,464)], a mixture of a Lewis acid and protonic acid [Unexamined Japanese Patent Application Laid-Open Specification No. 60-173016 (corresponding to U.S. Pat. No. 4,609,501)], a compound of Sc, Mo, Mn, Bi, Te or the like [Unexamined Japanese Patent Application Laid-Open Specification No. 1-265064 (corresponding to European Patent Publication No. 0 338 760 A1 and U.S. Pat. No. 5,034,557)], and ferric acetate (Unexamined Japanese Patent Application Laid-Open Specification No. 61-172852).

As a catalyst for use in the method for producing a diaryl carbonate by a same-species intermolecular transesterification, wherein an alkyl aryl carbonate is disproportionated to a diaryl carbonate and a dialkyl carbonate, there have been proposed various catalysts, which include for example, a Lewis acid and a transition metal compound which is capable of forming a Lewis acid [see Unexamined Japanese Patent Application Laid-Open Specification No. 51-75044 (corresponding to West German Patent Application Publication No. 2552907 and U.S. Pat. No. 4,045,464)], a polymeric tin compound [Unexamined Japanese Patent Application Laid-Open Specification No. 60-169444 (corresponding to U.S. Pat. No. 4,554,110 and West German Patent Application Publication No. 3445552)], a compound represented by the formula R—X(=O)OH (wherein X is selected from Sn and Ti, and R is selected from monovalent hydrocarbon residues) [Unexamined Japanese Patent Application Laid-Open Specification No. 60-169445 (corresponding to U.S. Pat. No. 4,552,704)], a mixture of a Lewis acid and protonic acid [Unexamined Japanese Patent Application Laid-Open Specification No. 60-173016 (corresponding to U.S. Pat. No. 4,609,501)], a lead catalyst (Unexamined Japanese Patent Application Laid-Open Specification No. 1-93560), a titanium or zirconium compound [Unexamined Japanese Patent Application Laid-Open Specification No. 1-265062 (corresponding to U.S. Pat. No. 5,166,393)], a tin compound [Unexamined Japanese Patent Application Laid-Open Specification No. 1-265063 (corresponding to European Patent Publication No. 0 338 760 A1 and U.S. Pat. No. 5,034,557)], and a compound of Sc, Mo, Mn, Bi, Te or the like [Unexamined Japanese Patent Application Laid-Open Specification No. 1-265064 (corresponding to European Patent Publication No. 0 338 760 A1 and U.S. Pat. No. 5,034,557)].

Another attempt for improving the yield of aromatic carbonates in these reactions consists in biasing the equilibrium toward the product system as much as possible, by modifying the mode of the reaction process. For example, there have been proposed a method in which by-produced methanol is distilled off together with an azeotrope forming agent by azeotropic distillation in the reaction of a dimethyl carbonate with phenol [see Unexamined Japanese Patent Application Laid-Open Specification No. 54-48732 (corresponding to West German Patent Application Publication No. 2736063 and U.S. Pat. No. 4,252,737) and Unexamined Japanese Patent Application Laid-Open Specification No. 61-291545], and a method in which by-produced methanol is removed by adsorbing the same onto a molecular sieve [Unexamined Japanese Patent Application Laid-Open Specification No. 58-185536 (corresponding to U.S. Pat. No. 4,410,464)].

Further, a method is known in which an apparatus comprising a reactor having provided on the top thereof a distillation column is employed in order to separate and distill off alcohols (by-produced in the course of the reaction) from a reaction mixture obtained in the reactor. [With respect to this method, reference can be made to, for example, Unexamined Japanese Patent Application Laid-Open Specification No. 56-123948 (corresponding to U.S. Pat. No. 4,182,726), Unexamined Japanese Patent Application Laid-Open Specification No. 56-25138, Unexamined Japanese Patent Application Laid-Open Specification No. 60-169444 (corresponding to U.S. Pat. No. 4,554,110), Unexamined Japanese Patent Application Laid-Open Specification No. 60-169445 (corresponding to U.S. Pat. No. 4,552,704), Unexamined Japanese Patent Application Laid-Open Specification No. 60-173016 (corresponding to U.S. Pat. No. 4,609,501), Unexamined Japanese Patent Application Laid-Open Specification No. 61-172852, Unexamined Japanese Patent Application Laid-Open Specification No. 61-291545, and Unexamined Japanese Patent Application Laid-Open Specification No. 62-277345.]

As more preferred methods for producing an aromatic carbonate, the present inventors previously developed a method in which a dialkyl carbonate and an aromatic hydroxy compound are continuously fed to a continuous multi-stage distillation column to effect a continuous transesterification reaction in the distillation column, while continuously withdrawing a low boiling point reaction mixture containing a by-produced alcohol from an upper portion of the distillation column by distillation and continuously withdrawing a high boiling point reaction mixture containing a produced alkyl aryl carbonate from a lower portion of the distillation column [see Unexamined Japanese Patent Application Laid-Open Specification No. 3-291257 (corresponding to U.S. Pat. No. 5,210,268 and European Patent Publication No. 0 461 274 B1)], and a method in which an alkyl aryl carbonate is continuously fed to a continuous multi-stage distillation column to effect a continuous transesterification reaction in the distillation column, while continuously withdrawing a low boiling point reaction mixture containing a byproduced dialkyl carbonate from an upper portion of the distillation column by distillation and continuously withdrawing a high boiling point reaction mixture containing a produced diaryl carbonate from a lower portion of the distillation column [see Unexamined Japanese Patent Application Laid-Open Specification No. 4-9358 (corresponding to U.S. Pat. No. 5,210,268 and European Patent Publication No. 0 461 274 B1)]. These methods for the first time realized efficient, continuous production of an aromatic carbonate. Thereafter, various methods for continuously producing an aromatic carbonate have further been developed, based on the above-mentioned methods developed by the present inventors. Examples of these methods include a method in which a catalytic transesterification reaction is performed in a column reactor [see Unexamined Japanese Patent Application Laid-Open Specification No. 6-41022 (corresponding to West German Patent Application Publication No. 4218061, European Patent Publication No. 0 572 870 A1 and U.S. Pat. No. 5,362,901), Unexamined Japanese Patent Application Laid-Open Specification No. 6-157424 (corresponding to West German Patent Application Publication No. 4226755, European Patent Publication No. 0 582 931 A1 and U.S. Pat. No. 5,334,742), Unexamined Japanese Patent Application Laid-Open Specification No. 6-184058 (corresponding to West German Patent Application Publication No. 4226756, European Patent Publication No. 0 582 930 A1 and U.S. Pat. No. 5,344,954)], a method in which use is made of a plurality of reactors which are connected in series [Unexamined Japanese Patent Application Laid-Open Specification No. 6-234707 (corresponding to West German Patent Application Publication No. 4301899, European Patent Publication No. 0 608 710 A1 and U.S. Pat. No. 5,463,102), and Unexamined Japanese Patent Application Laid-Open Specification No. 6-263694], a method in which a bubble tower reactor is used [Unexamined Japanese Patent Application Laid-Open Specification No. 6-298700 (corresponding to West German Patent Application Publication No. 4316428, European Patent Publication No. 0 614 877 A1 and U.S. Pat. No. 5,523,451)], and a method in which a vertically long reactor vessel is used (Unexamined Japanese Patent Application Laid-Open Specification No. 6-345697).

Also, there have been proposed methods for producing an aromatic carbonate stably for a prolonged period of time on a commercial scale. For example, Unexamined Japanese Patent Application Laid-Open Specification No. 6-157410 (corresponding to European Patent Publication No. 0 591 923 A1 and U.S. Pat. No. 5,380,908) discloses a method for producing aromatic carbonates from a dialkyl carbonate and an aromatic hydroxy compound, which comprises continuously supplying a mixture of raw materials and a catalyst to a reactor provided with a distillation column thereon to effect a transesterification reaction in the reactor, while continuously withdrawing a by-produced aliphatic alcohol from the reactor through the distillation column by distillation so as to keep the aliphatic alcohol concentration of the reaction system at 2% by weight or less. This prior art document describes that, by this method, continuous production of an aromatic carbonate can be performed in a stable manner. The object of this method is to avoid the deposition of the catalyst in the distillation column. However, the reason for the deposition of the catalyst in the distillation column to be able to be avoided by this method is very simple and resides in that the catalyst is not fed to the distillation column. This prior art document describes the effect that since the catalyst was fed only to the reactor, no clogging was observed in the distillation column. This document also describes that, when a catalyst is fed to the distillation column, clogging of a part of the distillation column occurs due to the deposition of the catalyst in the column. In view of the fact that, in this method, a catalyst is not fed to the distillation column, it is natural and not surprising that the deposition of the catalyst does not occur in the distillation column. In addition, in view of the fact that, in this method, a catalyst is not fed to the distillation column, it is also apparent that, by this method, it is impossible to efficiently conduct a reaction by feeding a catalyst to a distillation column (that is, it is impossible to conduct a reactive distillation by this method). Further, this prior art document does not teach or suggest any solution for the problem where a catalyst is deposited from a catalyst-containing liquid-phase mixture and the deposited catalyst adheres to a reactor, pipes, valves, means for separating the catalyst from the liquid phase, and the like in the system for transesterification. In this prior art document, the reason why the aliphatic alcohol concentration of the reaction system should be kept at 2% by weight or less is not explained. However, it is presumed that the aliphatic alcohol concentration requirement of 2% by weight or less is intended to bias the equilibrium toward the product system so that the reaction proceeds efficiently. In this prior art document, there is no description regarding the relationship between the aliphatic alcohol concentration and the deposition of a catalyst.

Unexamined Japanese Patent Application Laid-Open Specification No. 6-116210 (corresponding to European Patent Publication No. 0 591 923 A1 and U.S. Pat. No. 5,380,908) discloses a method for producing a diaryl carbonate from an alkyl aryl carbonate, which comprises continuously supplying a mixture of raw materials and a catalyst to a reactor provided with a distillation column thereon to effect a transesterification reaction in the reactor, while continuously withdrawing a by-produced dialkyl carbonate from the reactor through the distillation column by distillation so as to keep the dialkyl carbonate concentration of the reaction system at 2% by weight or less. This prior art document describes that, by this method, continuous production of a diaryl carbonate can be performed in a stable manner. The object of this method is to avoid the deposition of the catalyst in the distillation column. However, the reason why the deposition of the catalyst in the distillation column is able to be avoided by this method is very simple and resides in that the catalyst is not fed to the distillation column. This prior art document describes the effect that since the catalyst was fed only to the reactor, no clogging was observed in the distillation column. This document also describes that, when a catalyst is fed to the distillation column, clogging of a part of the distillation column occurs due to the deposition of the catalyst in the column. In view of the fact that, in this method, a catalyst is not fed to the distillation column, it is natural and not surprising that the deposition of the catalyst does not occur in the distillation column. In addition, in view of the fact that, in this method, a catalyst is not fed to the distillation column, it is also apparent that, by this method, it is impossible to efficiently conduct a reaction by feeding a catalyst to a distillation column (that is, it is impossible to conduct a reactive distillation by this method). Further, this prior art document does not teach or suggest any solution for the problem where a catalyst is deposited from a catalyst-containing liquid-phase mixture and the deposited catalyst adheres to a reactor, pipes, valves, means for separating the catalyst from the liquid phase, and the like in the system for transesterification.

When a catalyst is deposited from a catalyst-containing liquid-phase mixture and the deposited catalyst adheres to the inner walls of a reactor, pipes and the like, the reaction is adversely affected. That is, the deposited catalyst which is adhered to the inner walls of the reactor, pipes and the like cannot exhibit effective catalyst activity, even if it is present in the reactor. The deposition of the catalyst and the adhesion of the deposited catalyst to portions in the system for the transesterification means that the amount of the effective catalyst present in the reactor is decreased, so that the reaction cannot achieve favorable results.

SUMMARY OF THE INVENTION

In these situations, for solving the above-mentioned problems accompanying the prior art, the present inventors made extensive and intensive studies with a view toward developing an improvement in a process for producing an aromatic carbonate which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof. As a result, it has surprisingly been found that this task can be easily attained by conducting the transesterification while maintaining a weight ratio (WR) of at least one aromatic group-containing substance selected from the group consisting of an aromatic polyhydroxy compound and a residue thereof to the metal of the metal-containing catalyst at 2 or less, wherein the weight ratio (WR) is measured with respect to a catalyst-containing liquid-phase mixture in a system for the transesterification, and wherein the aromatic group-containing substance originates from the starting material, the reactant and/or a by-product of the transesterification. The present invention has been completed, based on the above finding.

Accordingly, it is a primary object of the present invention to provide an improved process for producing an aromatic carbonate, which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, which improved process can be used for producing an aromatic carbonate without suffering disadvantageous phenomena, such as the deposition of the catalyst from the catalyst-containing liquid-phase mixture and the adhesion of the deposited catalyst to the inner walls of the reactor, pipes and the like, so that the desired aromatic carbonate can be produced stably for a prolonged period of time.

The foregoing and other objects, features and advantages of the present invention will be apparent from the following detailed description and appended claims taken in connection with the accompanying drawings.

BRIEF DESCRIPTION OF THE DRAWINGS

In the drawings:

FIG. 4 is a diagram showing still a further example of systems for practicing the process of the present invention.

In FIG. 1 through FIG. 4, like parts or portions are designated by like numerals.

Figure 1:
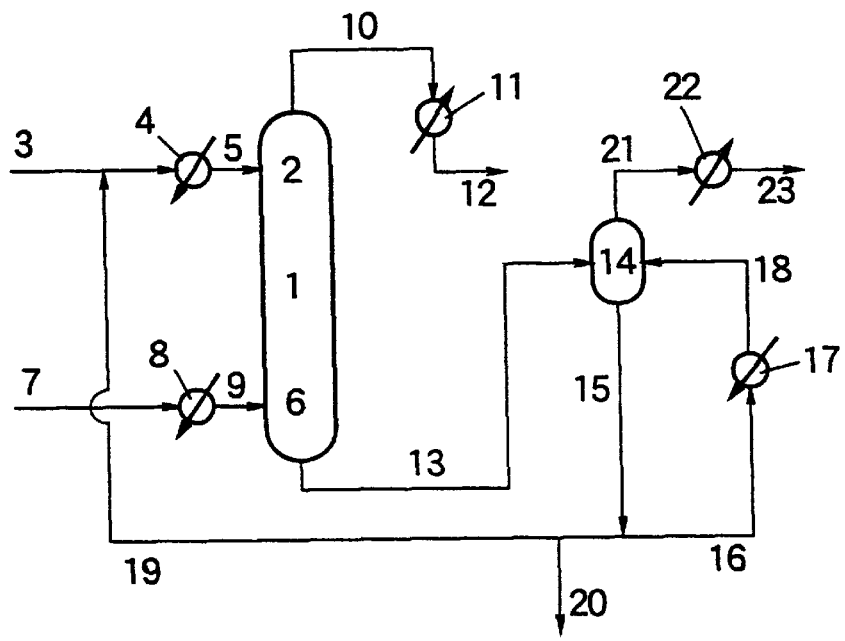
FIG. 1 is a diagram showing an example of systems for practicing the process of the present invention.

DESCRIPTION OF REFERENCE NUMERALS 1, 101: continuous multi-stage distillation column 2, 102: top of the continuous multi-stage distillation column 6, 106: bottom of the continuous multi-stage distillation column 24: distillation column 100: reaction vessel 3, 5, 7, 9, 10, 12, 13, 15, 16, 18, 19, 20, 21, 23, 25, 27, 28, 29, 30, 32, 105, 113, 115, 116, 118, 119, 120, 121, 123, 124, 125, 127, 128, 129, 130, 132, 224: conduit 4: preheater
8, 14, 114: evaporator
11, 22, 26, 122, 126: condenser
17, 31, 117, 131: reboiler

DETAILED DESCRIPTION OF THE INVENTION

In the present invention, there is provided a process for producing an aromatic carbonate which comprises transesterifying, in the presence of a metal-containing catalyst, a starting material selected from the group consisting of a dialkyl carbonate represented by the following formula (1):

$$R^1OCOR^1, \quad (1)$$
$$\parallel$$
$$O$$

an alkyl aryl carbonate represented by the following formula (2):

$$R^2OCOAr^2 \quad (2)$$
$$\parallel$$
$$O$$

and a mixture thereof with a reactant selected from the group consisting of an aromatic monohydroxy compound represented by the following formula (3):

$$Ar^1OH \quad (3),$$

an alkyl aryl carbonate represented by the following formula (4):

$$R^3OCOAr^3 \quad (4)$$
$$\parallel$$
$$O$$

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms and each of $Ar^1$, $Ar^2$ and $Ar^3$ independently represents an aromatic group having 5 to 30 carbon atoms, to thereby produce at least one aromatic carbonate selected from the group consisting of an alkyl aryl carbonate and a diaryl carbonate, which is selected in correspondence to the starting material and the reactant and represented by at least one formula selected from the group consisting of the following formulae (5) and (6):

$$ROCOAr \quad \text{and} \quad (5)$$
$$\parallel$$
$$O$$

$$ArOCOAr, \quad (6)$$
$$\parallel$$
$$O$$

wherein R and Ar are, respectively, selected from $R^1$, $R^2$ and $R^3$ and selected from $Ar^1$, $Ar^2$ and $Ar^3$ in correspondence to the starting material and the reactant,
characterized in that the transesterification is conducted while maintaining a weight ratio (WR) of at least one aromatic group-containing substance selected from the group consisting of an aromatic polyhydroxy compound and a residue thereof to the metal of the metal-containing catalyst at 2.0 or less, wherein the weight ratio (WR) is measured with respect to a catalyst-containing liquid-phase mixture in a system for the transesterification, and wherein the aromatic group-containing substance originates from at least one member selected from the group consisting of the starting material, the reactant and a by-product of the transesterification, the aromatic polyhydroxy compound being represented by the following formula (7):

$$Ar^4\text{-}(OH)_m \quad (7)$$

wherein $Ar^4$ represents an aromatic group having a valence of m, m represents an integer of 2 or more, and each —OH group is individually bonded to an arbitrary ring-carbon position of the $Ar^4$ group, and the residue of the aromatic polyhydroxy compound being represented by the following formula (8):

$$\text{-}(O)_n\text{-}Ar^4\text{-}(OH)_{m-n} \quad (8)$$

wherein $Ar^4$ and m are as defined above, n represents an integer of from 1 to m, and each of the —OH group and the —O— group is individually bonded to an arbitrary ring-carbon position of the $Ar^4$ group, and being present in such a form as chemically bonded to at least one member selected from the group consisting of the metal of the catalyst, an alkoxycarbonyl group derived from the dialkyl carbonate or the alkyl aryl carbonate, an aryloxycarbonyl group derived from the alkyl aryl carbonate or the diaryl carbonate, and a carbonyl group derived from the dialkyl carbonate, the alkyl aryl carbonate or the diaryl carbonate.

For an easy understanding of the present invention, the essential features and various preferred embodiments of the present invention are enumerated below.

1. In a process for producing an aromatic carbonate which comprises transesterifying, in the presence of a metal-containing catalyst, a starting material selected from the group consisting of a dialkyl carbonate represented by the following formula (1):

$$R^1OCOR^1, \quad (1)$$
$$\parallel$$
$$O$$

an alkyl aryl carbonate represented by the following formula (2):

$$R^2OCOAr^2 \quad (2)$$
$$\parallel$$
$$O$$

and a mixture thereof with a reactant selected from the group consisting of an aromatic monohydroxy compound represented by the following formula (3):

$$Ar^1OH \quad (3),$$

an alkyl aryl carbonate represented by the following formula (4):

$$R^3OCOAr^3 \quad (4)$$
$$\parallel$$
$$O$$

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms and each of $Ar^1$, $Ar^2$ and $Ar^3$ independently represents an aromatic group having 5 to 30 carbon atoms, to thereby produce at least one aromatic carbonate selected from the group consisting of an alkyl aryl carbonate and a diaryl carbonate, which is selected in correspondence to the starting material and the reactant and represented by at least one formula selected from the group consisting of the following formulae (5) and (6):

  (5)

  (6)

wherein R and Ar are, respectively, selected from $R^1$, $R^2$ and $R^3$ and selected from $Ar^1$, $Ar^2$ and $Ar^3$ in correspondence to the starting material and the reactant, the improvement being that the transesterification is conducted while maintaining a weight ratio (WR) of at least one aromatic group-containing substance selected from the group consisting of an aromatic polyhydroxy compound and a residue thereof to the metal of the metal-containing catalyst at 2.0 or less, wherein the weight ratio (WR) is measured with respect to a catalyst-containing liquid-phase mixture in a system for the transesterification, and wherein the aromatic group-containing substance originates from at least one member selected from the group consisting of the starting material, the reactant and a by-product of the transesterification, the aromatic polyhydroxy compound being represented by the following formula (7):

  (7)

wherein $Ar^4$ represents an aromatic group having a valence of m, m represents an integer of 2 or more, and each —OH group is individually bonded to an arbitrary ring-carbon position of the $Ar^4$ group, and the residue of the aromatic polyhydroxy compound being represented by the following formula (8):

  (8)

wherein $Ar^4$ and m are as defined above, n represents an integer of from 1 to m, and each of the —OH group and the —O— group is individually bonded to an arbitrary ring-carbon position of the $Ar^4$ group,
and being present in such a form as chemically bonded to at least one member selected from the group consisting of the metal of the catalyst, an alkoxycarbonyl group derived from the dialkyl carbonate or the alkyl aryl carbonate, an aryloxycarbonyl group derived from the alkyl aryl carbonate or the diaryl carbonate, and a carbonyl group derived from the dialkyl carbonate, the alkyl aryl carbonate or the diaryl carbonate.

2. The process according to item 1 above, wherein the aromatic polyhydroxy compound is at least one member selected from the group consisting of:

(A) an oxidation product of an aromatic monohydroxy compound as the reactant, (B) at least one member selected from the group consisting of a product produced by the Fries rear-rangement of a diaryl carbonate obtained by the transesterification and an oxidation product of the product and (C) at least one member selected from the group consisting of aromatic dihydroxy compounds derived from phenol as the reactant and represented by the following formula (9):

  (9)

wherein $Y^1$ represents a single bond, a divalent alkane group having 1 to 30 carbon atoms or a divalent group selected from —O—, —CO—, —S—, —$SO_2$—, —SO— and —COO—, and oxidation products of the aromatic dihydroxy compounds.

3. The process according to item 1 or 2 above, wherein the maintenance of the weight ratio (WR) at 2.0 or less is performed by using as the reactant an aromatic monohydroxy compound containing the aromatic polyhydroxy compound in a controlled concentration, and withdrawing a part of the catalyst-containing liquid-phase mixture out of the system for the transesterification.

4. The process according to item 3 above, wherein the aromatic monohydroxy compound has an aromatic polyhydroxy compound concentration of 400 ppm by weight or less.

5. The process according to item 1 above, which is for continuously producing the at least one aromatic carbonate, wherein a transesterification reaction mixture containing the at least one aromatic carbonate and containing the catalyst is continuously withdrawn from a reactor for the transesterification.

6. The process according to item 5 above, wherein the aromatic monohydroxy compound as the reactant comprises a mixture of a feedstock aromatic monohydroxy compound and an unreacted aromatic monohydroxy compound recycled from the reactor, wherein the feedstock aromatic monohydroxy compound has an aromatic polyhydroxy compound concentration of 400 ppm by weight or less.

7. The process according to item 5 or 6 above, wherein a part of the reaction mixture, containing the catalyst, withdrawn from the reactor is subjected to evaporation, and the resultant mixture having an increased catalyst concentration is at least partly withdrawn out of the system for the transesterification to thereby maintain the weight ratio (WR) at 2.0 or less.

8. The process according to any one of items 5 to 7 above, wherein the starting material and the reactant are continuously fed to a continuous multi-stage distillation column to effect a transesterification reaction therebetween in at least one phase selected from a liquid phase and a gas-liquid phase in the presence of the metal-containing catalyst in the distillation column, while continuously withdrawing a high boiling point reaction mixture containing the at least one aromatic carbonate in a liquid form from a lower portion of the distillation column and continuously withdrawing a low boiling point reaction mixture containing a by-product in a gaseous form from an upper portion of the distillation column by distillation.

The present invention is described below in detail.

The dialkyl carbonate to be used as a starting material in the present invention is represented by formula (1):

  (1)

wherein $R^1$ represents an alkyl group having 1 to 10 carbon atoms, an alicyclic group having 3 to 10 carbon atoms or an aralkyl group having 6 to 10 carbon atoms. Examples of $R^1$ include an alkyl group, such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; an alicyclic group, such as cyclopropyl, cyclobutyl, cyclopentyl, cyclohexyl and cycloheptyl; and an aralkyl group, such as benzyl, phenethyl (isomers), phenylpropyl (isomers), phenylbutyl (isomers) and methylbenzyl (isomers). The above-mentioned alkyl group, alicyclic group and aralkyl group may be substituted with a substituent, such as a lower alkyl group, a lower alkoxy group, a cyano group and a halogen atom, as long as the number of carbon atoms of the substituted group does not exceed 10, and may also contain an unsaturated bond.

As a dialkyl carbonate having such $R^1$, there may be mentioned for example, dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers). These dialkyl carbonates can also be used in mixture.

Of these dialkyl carbonates, a dialkyl carbonate containing as $R^1$ a lower alkyl group having 4 or less carbon atoms is preferably used. Most preferred is dimethyl carbonate.

The aromatic monohydroxy compound used as the reactant in the present invention is represented by formula (3):

$$Ar^1OH \qquad (3)$$

wherein $Ar^1$ represents an aromatic group having 5 to 30 carbon atoms, and the type of the compound is not limited as long as the hydroxyl group is directly bonded to the aromatic group.

Illustrative examples of $Ar^1$ in formula (3) include:

a phenyl group and various alkylphenyl groups, such as phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers,), pentylphenyl (isomers), hexylphenyl (isomers) and cyclohexylphenyl (isomers);

various alkoxyphenyl groups, such as methoxyphenyl (isomers), ethoxyphenyl (isomers) and butoxyphenyl (isomers);

various halogenated phenyl groups, such as fluorophenyl (isomers), chlorophenyl (isomers), bromophenyl (isomers), chloromethylphenyl (isomers) and dichlorophenyl (isomers);

various substituted phenyl groups represented by the formula (10):

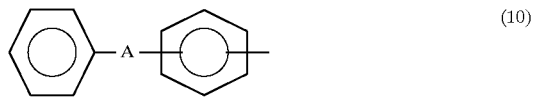

wherein A represents a bond, a divalent group, such as —O—, —S—, —CO— or —SO$_2$—, an alkylene group, a substituted alkylene group of the following formula:

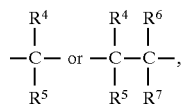

wherein each of $R^4$, $R^5$, $R^6$ and $R^7$ independently represents a hydrogen atom; or a lower alkyl group, a cycloalkyl group, an aryl group or an aralkyl group, which may be substituted with a halogen atom or an alkoxy group, or a cycloalkylene group of the following formula:

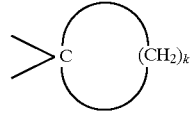

wherein k is an integer of from 3 to 11, and the hydrogen atoms may be replaced by a lower alkyl group, an aryl group, a halogen atom or the like, and the aromatic ring in formula (3) may be substituted with a substituent, such as a lower alkyl group, a lower alkoxy group, an ester group, a hydroxyl group, a nitro group, a halogen atom and a cyano group;

a naphthyl group and various substituted naphthyl groups, such as naphthyl (isomers), methylnaphthyl (isomers), dimethylnaphthyl (isomers), chloronaphthyl (isomers), methoxynaphthyl (isomers) and cyanonaphthyl (isomers); and various unsubstituted or substituted heteroaromatic groups, such as pyridyl (isomers), cumaryl (isomers), quinolyl (isomers), methylpyridyl (isomers), chloropyridyl (isomers), methylcumaryl (isomers) and methylquinolyl (isomers).

Preferred examples of aromatic monohydroxy compounds of formula (3) include phenol; various alkylphenols, such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols, such as methoxyphenol (isomers) and ethoxyphenol (isomers); various substituted phenols represented by the following formula (11):

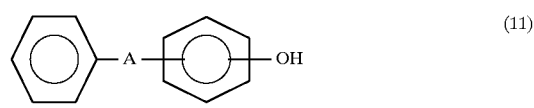

wherein A is as defined above;

naphthol (isomers) and various substituted naphthols; and heteroaromatic monohydroxy compounds, such as hydroxypyridine (isomers), hydroxycumarine (isomers) and hydroxyquinoline (isomers). These aromatic monohydroxy compounds can also be used in mixture.

Of these aromatic monohydroxy compounds, an aromatic monohydroxy compound containing as $Ar^1$ an aromatic group having 6 to 10 carbon atoms is preferably used in the present invention, and phenol is most preferred.

The alkyl aryl carbonate used as the starting material in the present invention is represented by the following formula (2):

  (2)

wherein $R^2$ may be identical with or different from $R^1$, and represents an alkyl group having 1 to 10 carbon atoms, an alicyclic group having 3 to 10 carbon atoms or an aralkyl group having 6 to 10 carbon atoms; and $Ar^2$ may be identical with or different from $Ar^1$, and represents an aromatic group having 5 to 30 carbon atoms. As $R^2$, there may be mentioned, for example, the same groups as set forth above for $R^1$. As $Ar^2$, there may be mentioned, for example, the same groups as set forth above for $Ar^1$.

Representative examples of alkyl aryl carbonate having these $R^2$ and $Ar^2$ include methyl phenyl carbonate, ethyl phenyl carbonate, propyl phenyl carbonate (isomers), allyl phenyl carbonate, butyl phenyl carbonate (isomers), pentyl phenyl carbonate (isomers), hexyl phenyl carbonate (isomers), heptyl phenyl carbonate (isomers), octyl tolyl carbonate (isomers), nonyl ethylphenyl carbonate (isomers), decyl butylphenyl carbonate (isomers), methyl tolyl carbonate (isomers), ethyl tolyl carbonate (isomers), propyl tolyl carbonate (isomers), butyl tolyl carbonate (isomers), allyl tolyl carbonate (isomers), methyl xylyl carbonate (isomers), methyl trimethylphenyl carbonate (isomers), methyl chlorophenyl carbonate (isomers), methyl nitrophenyl carbonate (isomers), methyl methoxyphenyl carbonate (isomers), methyl cumyl carbonate (isomers), methyl naphthyl carbonate (isomers), methyl pyridyl carbonate (isomers), ethyl cumyl carbonate (isomers), methyl benzoylphenyl carbonate (isomers), ethyl xylyl carbonate (isomers), benzyl xylyl carbonate (isomers). These alkyl aryl carbonates can also be used in mixture. Of these alkyl aryl carbonates, one containing as $R^2$ an alkyl group having 1 to 4 carbon atoms and as $Ar^2$ an aromatic group having 6 to 10 carbon atoms is preferably used, and methyl phenyl carbonate is most preferred.

The alkyl aryl carbonate used as the reactant in the present invention is represented by the following formula (4):

  (4)

wherein $R^3$ may be identical with or different from $R^1$ and $R^2$, and represents an alkyl group having 1 to 10 carbon atoms, as alicyclic group having 3 to 10 carbon atoms or an aralkyl group having 6 to 10 carbon atoms; and $Ar^3$ may be identical with or different from $Ar^1$ and $Ar^2$, and represents an aromatic group having 5 to 30 carbon atoms. As $R^3$, there may be mentioned, for example, the same groups as set forth above for $R^1$. As $Ar^3$, there may be mentioned, for example, the same groups as set forth above for $Ar^1$.

As alkyl aryl carbonates having these $R^3$ and $Ar^3$, there may be mentioned for example, those which are set forth above for alkyl aryl carbonates represented by the abovementioned formula (2).

Of these alkyl aryl carbonates, one containing as $R^3$ an alkyl group having 1 to 4 carbon atoms and as $Ar^3$ an aromatic group having 6 to 10 carbon atoms is preferably used, and methyl phenyl carbonate is most preferred.

The typical reactions which are involved in the process of the present invention are represented by the following formulae:

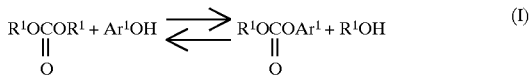  (I)

  (II)

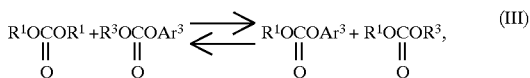  (III)

and

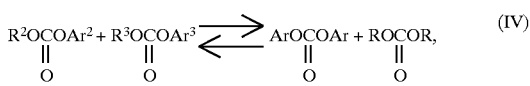  (IV)

wherein $R^1$, $R^2$, $R^3$, $Ar^1$, $Ar^2$ and $Ar^3$ are as defined above, each of Ar's appearing in formula (IV) independently represents $Ar^2$ or $Ar^3$, and each of R's appearing in formula (IV) independently represents $R^2$ or $R^3$, and wherein when $R^2=R^3$ and $Ar^2=Ar^3$ in formula (IV), the reaction is a same-species intermolecular transesterification reaction generally known as a disproportionation reaction.

When each of the reactions of formulae (I), (II), (III) and (IV) is performed according to the process of the present invention, dialkyl carbonates or alkyl aryl carbonates as the starting materials for the reaction can be used individually or in mixture and aromatic monohydroxy compounds or alkyl aryl carbonates as the reactants for the reaction can be used individually or in mixture.

When $R^2=R^3=R$ and $Ar^2=Ar^3=Ar$ in the transesterification reaction of formula (IV), a diaryl carbonate and a dialkyl carbonate can be obtained by a same-species intermolecular transesterification reaction of a single type of alkyl aryl carbonate. This is a preferred embodiment of the present invention.

Further, when $R^1=R^2=R^3=R$ and $Ar^1=Ar^2=Ar^3=Ar$ in formulae (I) and (IV), by combining the reaction of formula (I) with the reaction of formula (IV), a diaryl carbonate can be obtained from a dialkyl carbonate and an aromatic monohydroxy compound through an alkyl aryl carbonate as shown in formulae (V) and (VI). This is an especially preferred embodiment of the present invention.

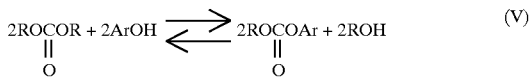  (V)

  (VI)

Recycling of the dialkyl carbonate by-produced in the reaction of formula (VI) as the starting material for the reaction of formula (V) results in the formation of 1 mol. of a diaryl carbonate and 2 mol. of an aliphatic alcohol from 1 mol. of a dialkyl carbonate and 2 mol. of an aromatic monohydroxy compound.

When $R=CH_3$ and $Ar=C_6H_5$ in the above formulae (V) and (VI), diphenyl carbonate, which is an important raw material for a polycarbonate and an isocyanate, can be readily obtained from dimethyl carbonate, which is the simplest form of a dialkyl carbonate, and phenol. This is especially important.

The metal-containing catalyst used in the present invention is one capable of promoting the reactions of formulae (I) to (IV). As such metal-containing catalysts, there may be mentioned for example:

(lead compounds)
lead oxides, such as PbO, $PbO_2$ and $Pb_3O_4$; lead sulfides, such as PbS and $Pb_2S$; lead hydroxides, such as $Pb(OH)_2$ and $Pb_2O_2(OH)_2$; plumbites, such as $Na_2PbO_2$, $K_2PbO_2$, $NaHPbO_2$ and $KHPbO_2$; plumbates, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO_3.Pb(OH)_2$; lead salts of organic acids, and carbonates and basic salts thereof, such as $Pb(OCOCH_3)_2$, $Pb(OCOCH_3)_4$ and $Pb(OCOCH_3)_2.PbO.3H_2O$; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ wherein Bu represents a butyl group and Ph represents a phenyl group; alkoxylead compounds and aryloxylead compounds, such as $Pb(OCH_3)_2$, $(CH_3O)Pb(OPh)$ and $Pb(OPh)_2$; lead alloys, such as Pb—Na, Pb—Ca, Pb—Ba, Pb—Sn and Pb—Sb; lead minerals, such as galena and zinc blende; and hydrates of these lead compounds;

(copper family metal compounds)
salts or complexes of copper family metals, such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, $Ag(bullvalene)_3NO_3$, $[AuC{\equiv}C{-}C(CH_3)_3]_n$ and $[Cu(C_7H_8)Cl]_4$ wherein OAc represents an acetyl group and acac represents an acetylacetone chelate ligand;

(alkali metal complexes)
alkali metal complexes, such as Li(acac) and $LiN(C_4H_9)_2$;

(zinc complexes)
zinc complexes, such as $Zn(acac)_2$;

(cadmium complexes)
cadmium complexes, such as $Cd(acac)_2$;

(iron family metal compounds)
iron family metal complexes, such as $Fe(C_{10}H_8)(CO)_5$, $Fe(CO)_5$, $Fe(C_3H_6)(CO)_3$, $Co(mesitylene)_2(PEt_2Ph)_2$, $CoC_5F_5(CO)_2$, $Ni{-}\pi{-}C_5H_5NO$ and ferrocene;

(zirconium complexes)
zirconium complexes, such as $Zr(acac)_4$ and zirconocene;

(Lewis acids and Lewis acid-forming compounds)
Lewis acids and Lewis acid-forming transition metal compounds, such as $AlX_3$, $TiX_3$, $TiX_4$, $VOX_3$, $VX_5$, $ZnX_2$, $FeX_3$ and $SnX_4$ wherein X represents a halogen atom, an acetoxy group, an alkoxy group or an aryloxy group; and (organotin compounds)
organotin compounds, such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and BuSnO(OH).

These catalysts are effective even when they are reacted with an organic compound present in the reaction system, such as an aliphatic alcohol, an aromatic monohydroxy compound, an alkyl aryl carbonate, a diaryl carbonate and a dialkyl carbonate. Those which are obtained by heat-treating these catalysts together with a starting material, a reactant and/or a reaction product thereof prior to the use in the process of the present invention can also be used.

It is preferred that the metal-containing catalyst have high solubility in the liquid phase of the reaction system. Preferred examples of metal-containing catalysts include Pb compounds, such as PbO, $Pb(OH)_2$ and $Pb(OPh)_2$; Ti compounds, such as $TiCl_4$ and $Ti(OPh)_4$; Sn compounds, such as $SnCl_4$, $Sn(OPh)_4$, $Bu_2SnO$ and $Bu_2Sn(OPh)_2$; Fe compounds, such as $FeCl_3$, $Fe(OH)_3$ and $Fe(OPh)_3$; and reaction products of the above metal compounds with the starting material, the reactant or a product formed by the transesterification reaction of the starting material with the reactant.

In the present invention, it is possible to use a metal-containing catalyst which is not completely soluble in the liquid phase of the reaction system. In this case, from a practical viewpoint, it is important that the catalyst be in a form (for example, a slurry form) such that the catalyst can exert satisfactory catalyst activity in the reaction system.

As mentioned above, in the present invention, the aromatic polyhydroxy compound and a residue thereof (which originate from at least one member selected from the group consisting of the starting material, the reactant and a by-product of the transesterification) are, respectively, represented by the following formulae (7) and (8):

  (7)

wherein $Ar^4$ represents an aromatic group having a valence of m, m represents an integer of 2 or more, and each —OH group is individually bonded to an arbitrary ring-carbon position of the $Ar^4$ group, and

  (8)

wherein $Ar^4$ and m are as defined above, n represents an integer of from 1 to m, and each of the —OH group and the —O— group is individually bonded to an arbitrary ring-carbon position of the $Ar^4$ group.

The residue of the aromatic polyhydroxy compound is present in such a form as chemically bonded, at the —O— group thereof, to at least one member selected from the group consisting of the metal of the catalyst, an alkoxycarbonyl group derived from the dialkyl carbonate or the alkyl aryl carbonate, an aryloxycarbonyl group derived from the alkyl aryl carbonate or the diaryl carbonate, and a carbonyl group derived from the dialkyl carbonate, the alkyl aryl carbonate or the diaryl carbonate.

Illustrative examples of the $Ar^4$ groups in formulae (7) and (8) above include aromatic groups represented by the following formulae (12), (13), (14), (15) and (16):

  (12)

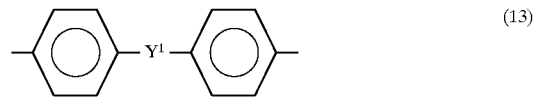  (13)

wherein $Y^1$ is as defined above;

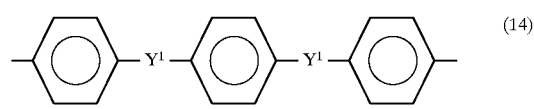  (14)

wherein each of two $Y^1$'s is as defined above, and two $Y^1$'s may be the same-or different;

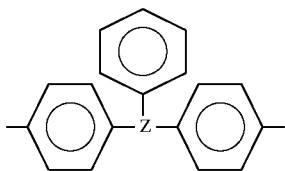

(15)

wherein Z represents a trivalent group, such as a $C_1$–$C_{30}$ trivalent alkane group or a trivalent aromatic group; and at least one hydrogen atom of each aromatic ring may be replaced with a substitutent, such as a halogen atom, a $C_1$–$C_{30}$ alkyl group, a $C_1$–$C_{30}$ alkoxy group, a phenyl group, a phenoxy group, a vinyl group, a cyano group, an ester group, an amido group, a nitro group or the like; and

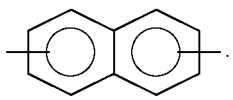

(16)

Examples of these aromatic polyhydroxy compounds include hydroquinone, resorcin, catechol, trihydroxybenzene (isomers), bis(hydroxyphenyl)propane (isomers), bis(hydroxyphenyl)methane (isomers), bis(hydroxyphenyl)ether (isomers), bis(hydroxyphenyl)ketone (isomers), bis(hydroxyphenyl)sulfone (isomers), bis(hydroxyphenyl)sulfide (isomers), dihydroxy diphenyl (isomers), bis(dihydroxyphenyl)methane (isomers), 2-hydroxyphenyl hydroxypropyl phenol, dihydroxy (hydroxyphenyl diphenyl) (isomers), tri-(hydroxyphenyl)ethane (isomers), tri-(hydroxyphenyl)benzene (isomers), dihydroxynaphthalene (isomers) and trihydroxynaphthalene (isomers).

Of these aromatic polyhydroxy compounds and residues thereof, those which are likely to be present in the system for the transestirification for the production of an aromatic carbonate are especially important in the present invention. As such an important aromatic polyhydroxy compound, there can be mentioned at least one member selected from the group consisting of:

(A) an oxidation product of an aromatic monohydroxy compound as the reactant, (B) at least one member selected from the group consisting of a product produced by the Fries rearrangement of a diaryl carbonate obtained by the transesterification and oxidation products of the product and (C) at least one member selected from the group consisting of aromatic dihydroxy compounds derived from phenol as the reactant and represented by the following formula (9):

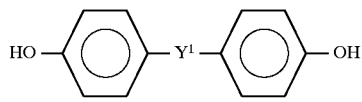

(9)

wherein $Y^1$ represents a single bond, a divalent alkane group having 1 to 30 carbon atoms or a divalent group selected from —O—, —CO—, —S—, —SO$_2$—, —SO— and —COO—, and oxidation products of the aromatic dihydroxy compounds.

As examples of the oxidation product (A) of an aromatic monohydroxy compound, compounds represented by the following formulae (17) and (18) can be mentioned.

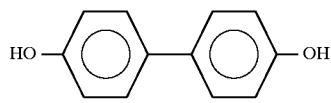

(17)

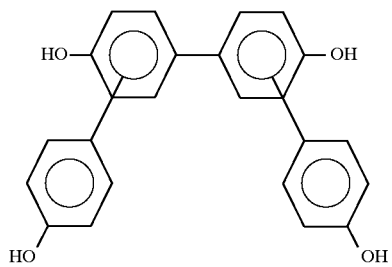

(18)

As examples of the product (B) produced by the Fries rearrangement of a diaryl carbonate, compounds represented by the following formulae (19), (20) and (21) can be mentioned.

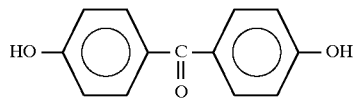

(19)

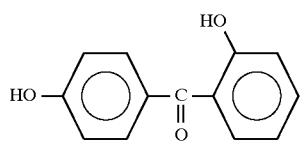

(20)

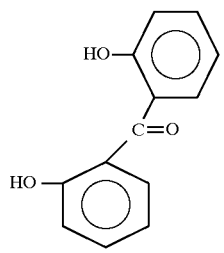

(21)

As examples of oxidation products of the above-mentioned product (B) produced by the Fries rearrangement of a diaryl carbonate and represented by formula (19), compounds represented by the following formulae (22) and (23) can be mentioned. Also, as examples of respective oxidation products of the above-mentioned products (B) represented by formulae (20) and (21), compounds represented by the following formulae (24) and (25) can be mentioned.

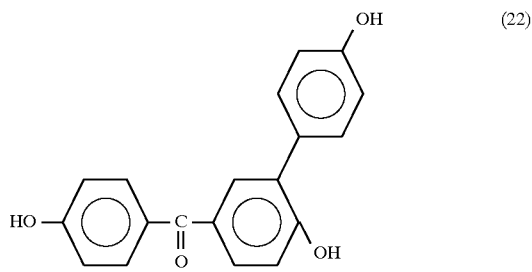

(22)

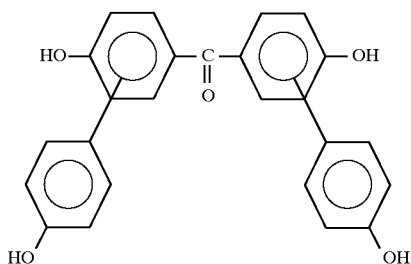
(23)

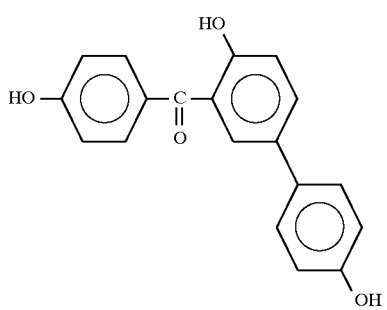
(24)

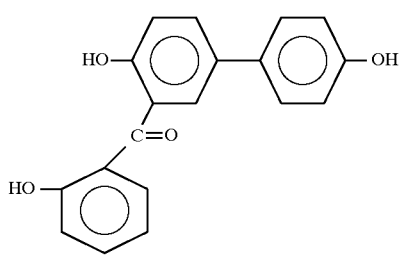
(25)

As an example of the aromatic dihydroxy compound (C) represented by formula (9), a compound represented by the following formula (26) can be mentioned.

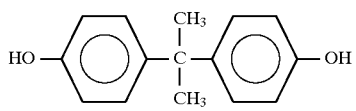
(26)

As examples of oxidation products of the above-mentioned aromatic dihydroxy compound (C) represented by formula (26), compounds represented by the following formulae (27) and (28) can be mentioned.

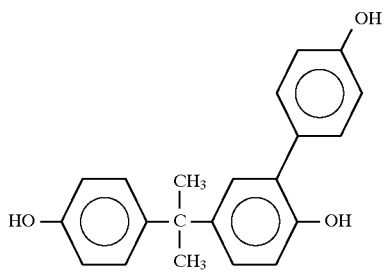
(27)

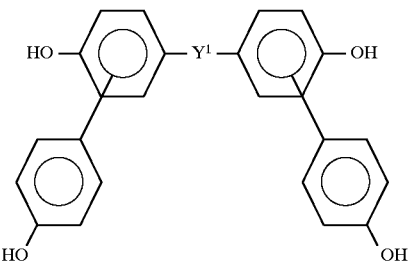
(28)

wherein $Y^1$ is as defined above.

The reason why the above-mentioned oxidation product (A) of an aromatic monohydroxy compound is likely to be present in the system for the transesterification for the production of an aromatic carbonate, for example, is that such an oxidation product is formed by the oxidation of an aromatic monohydroxy compound with a very small amount of oxygen which occasionally enters the system for the transesterification, or that such an oxidation product is occasionally present as a contaminant of an aromatic monohydroxy compound as a raw material and enters the system together with the raw material. Representative examples of type (A) oxidation products, namely, oxidation products of aromatic monohydroxy compounds include dihydroxybenzene (isomers), dihydroxy diphenyl (isomers), and the like.

Product (B) produced by the Fries rearrangement of a diaryl carbonate is likely to be formed as a by-product in the production of the diaryl carbonate. Examples of products (B) include 2,2'-dihydroxybenzophenone, 2,4'-dihydroxybenzophenone and 4,4'-dihydroxybenzophenone.

The aromatic dihydroxy compound (C) is a compound which is usually used as a monomer for the production of an aromatic polycarbonate. An aromatic polycarbonate can be produced by a transesterification of the above-mentioned aromatic dihydroxy compound (C) with a diaryl carbonate, wherein an aromatic monohydroxy compound is by-produced. When such a by-produced aromatic monohydroxy compound is used as a raw material in the process of the present invention, the aromatic dihydroxy compound (C) is likely to be introduced into the system for the transesterification for the production of an aromatic carbonate. Examples of aromatic dihydroxy compounds (C) include 2,2-bis-(4-hydroxyphenyl)propane, and the like.

Further, 2,2-bis-(4-hydroxyphenyl)propane usually contains aromatic polyhydroxy compounds represented by the following formulae, which compounds are also included in the aromatic polyhydroxy compound defined in the present invention.

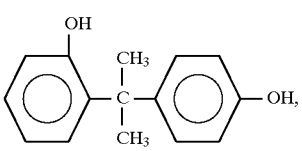

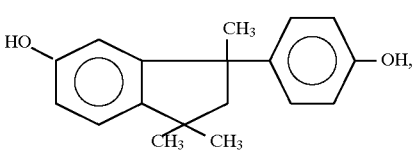

-continued

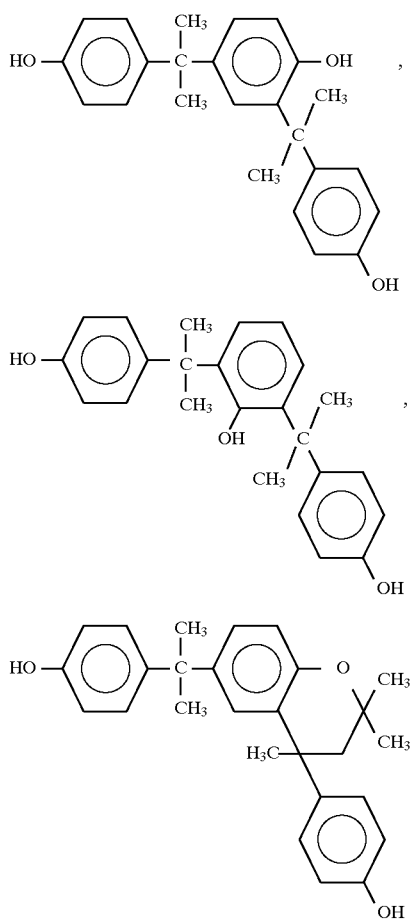

In the process of the present invention, it is essential to conduct a transesterification while maintaining a weight ratio (WR) of at least one aromatic group-containing substance selected from the group consisting of an aromatic polyhydroxy compound and a residue thereof to the metal of the metal-containing catalyst at 2.0 or less, wherein the weight ratio (WR) is measured with respect to a catalyst-containing liquid-phase mixture in a system for the transesterification. The above-mentioned weight ratio (WR) is preferably 1.0 or less, more preferably 0.5 or less. The term "system for the transesterification" means a system which includes not only the reactor, but also the pipes and devices provided in connection with the reactor, such as a device for the recovering and recycling or recirculating of the catalyst, and the like. In the present invention, the term "catalyst-containing liquid-phase mixture" means a catalyst-containing liquid material to be fed to the reactor, a catalyst-containing reaction mixture in the reactor, a catalyst-containing reaction mixture withdrawn from the reactor, a liquid material having an increased catalyst concentration which is obtained by subjecting to evaporation a part of the catalyst-containing reaction mixture withdrawn from the reactor, and the like. In the catalyst-containing liquid-phase mixture, either the catalyst may be completely dissolved, or it need not be completely dissolved. In the case of the latter, the catalyst-containing liquid-phase mixture is in the form of a slurry. In the present invention, when the catalyst-containing reaction mixture is in the form of a slurry (which contains insoluble matters), such a slurry including insoluble matters is also referred to as a "catalyst-containing liquid-phase mixture". With respect to the above-mentioned weight ratio (WR), it has been found that, when the WR exceeds 2.0, disadvantageous phenomena, such as the deposition of the metal-containing catalyst from the catalyst-containing liquid-phase mixture and the adhesion of the deposited catalyst to the inner walls of the reactor, pipes and the like occur, so that the reaction becomes unstable and hence cannot achieve favorable results. The reason for this has not yet been elucidated, but is considered to be as follows. When the above-mentioned weight ratio (WR) exceeds 2.0, an insoluble substance having a crosslinked structure is formed by a crosslinking reaction between the metal of the metal-containing catalyst and the aromatic polyhydroxy compound and deposited from the liquid-phase mixture, wherein the deposited substance has strong adhesiveness to the inner walls of the reactor, pipes, and the like.

In the process of the present invention for producing an aromatic carbonate, the aromatic monohydroxy compound used as a reactant frequently comprises two types of compounds, i.e., a fresh feedstock aromatic monohydroxy compound and an unreacted aromatic monohydroxy compound recycled from the reactor. There is no particular limitation with respect to the ratio of the fresh feedstock aromatic monohydroxy compound to the unreacted aromatic monohydroxy compound recycled from the reactor; however, the weight ratio of the fresh feedstock aromatic monohydroxy compound to the unreacted aromatic monohydroxy compound recycled from the reactor is generally in the range of from 100:0 to 0.0001:99.9999. In the present invention, for maintaining the weight ratio (WR) of the at least one aromatic group-containing substance to the metal of the metal-containing catalyst at 2.0 or less as measured with respect to a catalyst-containing liquid-phase mixture in the system for the transesterification, it is preferred that the fresh feedstock aromatic monohydroxy compound have an aromatic polyhydroxy compound concentration of 400 ppm by weight or less, more preferably 300 ppm by weight or less, most preferably 200 ppm by weight or less.

As a method for controlling the concentration of the at least one aromatic group-containing substance in the catalyst-containing liquid-phase mixture so as to maintain the weight ratio (WR) within the range as defined in the present invention, it is preferred to withdraw a part of the catalyst-containing liquid-phase mixture out of the system for the transesterification. For example, when the process of the present invention comprises the steps of subjecting to evaporation a part of the catalyst-containing-liquid-phase mixture withdrawn from the reactor and recycling the resultant catalyst-containing liquid-phase mixture having an increased catalyst concentration to the reactor, the accumulation of the aromatic group-containing substance in the system can be effectively avoided by withdrawing at least a part of the resultant evaporation-concentrated liquid-phase mixture (having an increased catalyst concentration) out of the system for the transesterification. Further, the accumulation of the aromatic group-containing substance in the system for the transesterification can also be avoided by a method in which occasional entry of air into the system is suppressed to a level as low as possible, to thereby suppress the formation of an aromatic polyhydroxy compound as an oxidization product of the aromatic monohydroxy compound.

In the process of the present invention, it is preferred that the amount of the aromatic polyhydroxy compound in each of the starting material and the reactant be as small as possible.

Further, when the amount of such an aromatic group-containing substance in the system for the transesterification is considerably large (due to the introduction of such a substances as impurities of the starting material to the system together with the starting material or the reactant, or due to the formation of such a substance in the system by side reactions), for example, in the process for continuously producing a desired aromatic polycarbonate, it is preferred to start the above-mentioned withdrawal of at least a part of the evaporation-concentrated, catalyst-containing liquid-phase mixture out of the system for the transesterification at an early stage and/or to increase the withdrawal amount, depending on the amount of aromatic group-containing substance present in the system, so as to avoid the accumulation of the aromatic group-containing substance in the system. For enabling such a withdrawal of the evaporation-concentrated, catalyst-containing liquid-phase mixture to be conducted properly, it is preferred to use, for example, the following method. A sampling nozzle is provided on a pipe connected to the outlet of the reactor, and samples of a catalyst-containing liquid-phase mixture withdrawn from the reactor are taken at predetermined intervals through the sampling nozzle. By measuring the amount of the aromatic group-containing substance in each sample and monitoring the changes in the amount of the aromatic group-containing substance in the samples, suitable timing for starting the withdrawal and a suitable withdrawal amount can be determined so that the weight ratio (WR) of the aromatic group-containing substance to the metal of the metal-containing catalyst in the catalyst-containing liquid-phase mixture can be maintained within the range defined in the present invention.

An example of the above-mentioned operation for withdrawing the catalyst-containing liquid-phase mixture out of the system for the transesterification is explained below, referring to FIG. 1. FIG. 1 shows an example of systems for practicing the process of the present invention for producing an aromatic carbonate using a continuous multi-stage distillation column. In the system shown in FIG. 1, a mixture of dimethyl carbonate, phenol and a catalyst is continuously fed in liquid form from conduit 3 to continuous multi-stage distillation column 1 at top 2 thereof (which column 1 has sieve trays therein) through preheater 4 and conduit 5, thereby allowing the mixture to flow down inside of multi-stage distillation column 1. Simultaneously, dimethyl carbonate is introduced from conduit 7 into evaporator 8, in which the evaporation of the dimethyl carbonate is performed, and the resultant gas is continuously fed to bottom 6 of distillation column 1 through conduit 9, so that a transesterification reaction is conducted while effecting distillation. Gas (containing methanol and dimethyl carbonate) distilled from column top 2 is led into condenser 11 through conduit 10, in which the gas is condensed. The resultant condensate is continuously withdrawn through conduit 12. A reaction mixture (containing the produced methyl phenyl carbonate, the catalyst, and an aromatic polyhydroxy compound and a residue thereof, which residue is chemically bonded to, for example, carbonyl groups derived from the carbonates and/or to the metal of the catalyst) is continuously withdrawn from column bottom 6, and led through conduit 13 into evaporator 14, in which the methyl phenyl carbonate is evaporated to thereby obtain an evaporation-concentrated liquid (containing the catalyst, the aromatic polyhydroxy compound and the residue thereof). A part of the obtained concentrated liquid is led into reboiler 17 through conduits 15 and 16 and recycled into evaporator 14 through conduit 18. The rest of the concentrated liquid is recycled into distillation column 1 through conduits 15 and 19. An evaporated gas (containing the methyl phenyl carbonate) from evaporator 14 is led into condenser 22 through conduit 21, in which the gas is condensed. The resultant condensate is withdrawn from condenser 22 through conduit 23. The concentrated liquid, which is being recycled into distillation column 1 through conduit 19 as mentioned above, is partly withdrawn out of the system for the transesterification through conduit 20. By the withdrawal of a part of the concentrated liquid through conduit 20, the aromatic group-containing substance is at least partly withdrawn out of the system for the transesterification, so that the weight ratio (WR) of the aromatic group-containing substance to the metal of the catalyst in the catalyst-containing liquid-phase mixture in the system for the transesterification can be maintained at 2.0 or less. In the above system, the catalyst is fed to distillation column 1 through conduit 3 in such an amount as to compensate for the amount of the catalyst withdrawn from conduit 20, so that the catalyst concentration of the catalyst-containing liquid-phase mixture in the system for the transesterification is maintained at a predetermined level. There is no particular limitation with respect to the amount of the concentrated liquid withdrawn out of the system for the transesterification. However, the concentrated liquid is generally withdrawn in such an amount that the weight ratio of the concentrated liquid withdrawn out of the system for the transesterification to an aromatic carbonate to be produced is in the range of from $10^{-8}$ to 0.1, preferably from $10^{-6}$ to 0.05.

With respect to the lower limit of the content of the aromatic group-containing substance in the catalyst-containing liquid-phase mixture in the system for the transesterification, there is no particular limitation. However, when it is attempted to obtain a catalyst-containing liquid-phase mixture having an extremely small content of the aromatic group-containing substance, disadvantages arise in that a burden on the separation and purification equipment for the starting material and reactant to be fed to the system for the transesterification becomes large, and that the amount of the catalyst-containing liquid-phase mixture which must be withdrawn out of the system becomes too large. Therefore, the weight ratio (WR) of the aromatic group-containing substance to the metal of the catalyst in the catalyst-containing liquid-phase mixture in the system for the transesterification is generally not smaller than $10^{-9}$, preferably not smaller than $10^{-8}$.

The process of the present invention for producing an aromatic carbonate may either be conducted in a batchwise manner or in a continuous manner. It is preferred that an aromatic carbonate be produced in a continuous manner. For example, an aromatic carbonate can be continuously produced by a method in which a starting material and a reactant are continuously fed to a reactor to effect a transesterification reaction therebetween in at least one phase selected from a liquid phase and a gas-liquid phase in the presence of a metal-containing catalyst in the reactor, while continuously withdrawing a high boiling point reaction mixture containing the produced aromatic carbonate or aromatic carbonate mixture in liquid form from a lower portion of the reactor and continuously withdrawing a low boiling point reaction mixture containing a by-product in gaseous form from an upper portion of the reactor by distillation.

Figure 2:
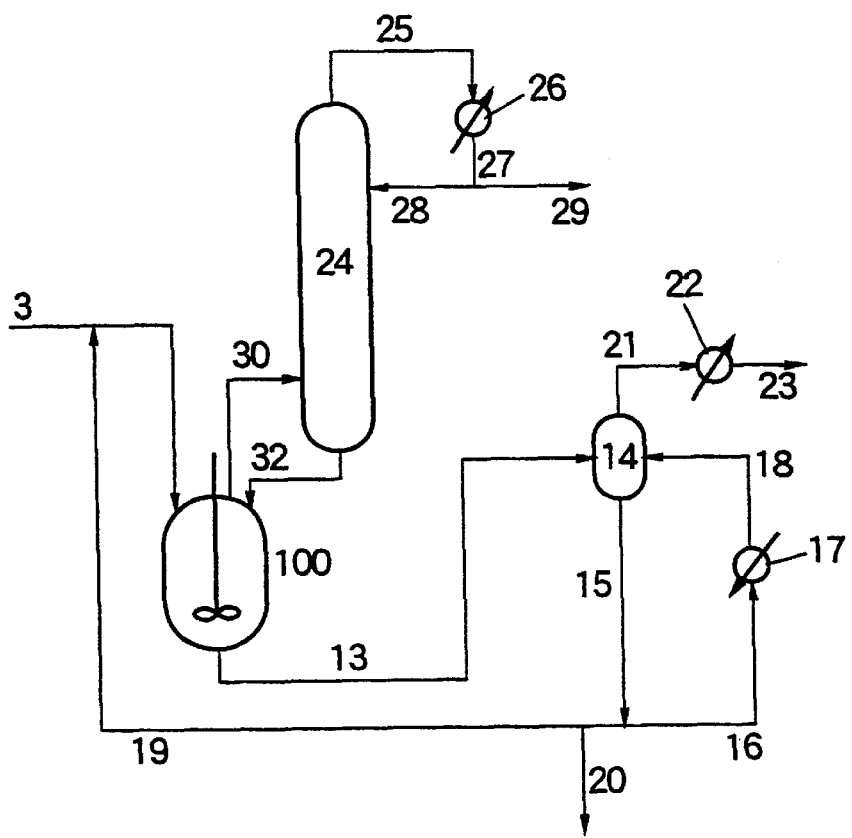
FIG. 2 is a diagram showing another example of systems for practicing the process of the present invention.

One illustrative example of systems for practicing the process for continuously producing an aromatic carbonate is shown in FIG. 2, wherein reaction vessel 100 equipped with a stirrer is used. In the process using the system of FIG. 2, a starting material and a reactant are continuously fed to reaction vessel 100 from conduit 3 to thereby effect a transesterification reaction therebetween in at least one phase selected from a liquid phase and a gas-liquid phase in the presence of a metal-containing catalyst in reaction vessel 100, while continuously withdrawing a high boiling point reaction aromatic containing a produced aromatic carbonate and the catalyst from a bottom portion of reaction vessel 100 through conduit 13 and continuously withdrawing a low boiling point reaction mixture containing a by-product in gaseous form from an upper portion of reaction vessel 100 through conduit 30, distillation column 24 and conduit 29.

Another illustrative example of systems for practicing the process for continuously producing an aromatic carbonate is shown in FIG. 1, wherein continuous multi-stage distillation column 1 is used as a reactor. In the process using the system of FIG. 1, a starting material and a reactant are continuously fed to continuous multi-stage distillation column 1 at top 2 thereof and/or bottom 6 thereof to effect a transesterification reaction therebetween in at least one phase selected from a liquid phase and a gas-liquid phase in the presence of a metal-containing catalyst in continuous multi-stage distillation column 1, while continuously withdrawing a high-boiling point reaction mixture containing a produced aromatic carbonate and the catalyst from a lower portion of distillation column 1 through conduit 13 and continuously withdrawing a low boiling point reaction mixture containing a by-product in gaseous form from an upper portion of distillation column 1 through conduit 10, condenser 11 and conduit 12 by distillation.

As apparent from the above, there is no particular limitation with respect to the type of the reactor to be used in the process of the present invention, and various types of conventional reactors, such as an agitation type reactor, a multi-stage agitation type reactor and a multi-stage distillation column, can be used. These types of reactors can be used individually or in combination, and may be used either in a batchwise process or a continuous process. From the viewpoint of efficiently biasing the equilibrium toward the product system, a multi-stage distillation column is preferred, and a continuous process using a multi-stage distillation column is especially preferred. There is no particular limitation with respect to the multistage distillation column to be used in the present invention as long as it is a distillation column having a theoretical number of stages of distillation of two or more and which can be used for performing continuous distillation. Examples of such multi-stage distillation columns include plate type columns using a tray, such as a bubble-cap tray, a perforated tray, a valve tray and a counterflow tray, and packed type columns packed with various packings, such as a Raschig ring, a Lessing ring, a Pall ring, a Berl saddle, an Intelox saddle, a Dixon packing, a McMahon packing, a Heli pack, a Sulzer packing and Mellapak. In the present invention, any of the columns which are generally used as a multi-stage distillation column can be utilized. Further, a mixed type of plate column and packed column comprising both a plate portion and a portion packed with packings, can also be preferably used. With respect to a process for continuously producing an aromatic carbonate using a multi-stage distillation column, reference can be made to, for example, U.S. Pat. No. 5,210,268 and EP Patent Publication No. 0 461 274 B1 corresponding to the above U.S. patent.

In one preferred embodiment of the present invention, in which the continuous production of an aromatic carbonate is conducted using a multi-stage distillation column, a starting material and a reactant are continuously fed to a continuous multi-stage distillation column to effect a transesterification reaction therebetween in at least one phase selected from a liquid phase and a gas-liquid phase in the presence of a metal-containing catalyst in the distillation column, while continuously withdrawing a high boiling point reaction mixture containing a produced aromatic carbonate or aromatic carbonate mixture in liquid form from a lower portion of the distillation column and continuously withdrawing a-low boiling point reaction mixture containing a by-product in gaseous form from an upper portion of the distillation column by distillation.

The amount of the catalyst used in the present invention varies depending on the type thereof, the types and weight ratio of the starting material and the reactant, the reaction conditions, such as reaction temperature and reaction pressure, and the like. Generally, the amount of the catalyst is in the range of from 0.0001 to 30% by weight, based on the total weight of the starting material and the reactant.

The reaction time (or the residence time when the reaction is continuously conducted) for the transesterification reaction in the present invention is not specifically limited, but it is generally in the range of from 0.001 to 50 hours, preferably from 0.01 to 10 hours, more preferably from 0.05 to 5 hours.

The reaction temperature varies depending on the types of the starting material and reactant, but is generally in the range of from 50° to 350° C., preferably from 100° to 280° C. The reaction pressure varies depending on the types of the starting material and reactant and the reaction temperature, and it may be any of a reduced pressure, an atmospheric pressure and a superatmospheric pressure. However, the reaction pressure is generally in the range of from 0.1 mmHg to 200 kg/cm$^2$.

In the present invention, it is not necessary to use a solvent. However, for the purpose of facilitating the reaction operation, an appropriate inert solvent, such as an ether, an aliphatic hydrocarbon, an aromatic hydrocarbon, a halogenated aliphatic hydrocarbon or a halogenated aromatic hydrocarbon, may be used as a reaction solvent.

BEST MODE FOR CARRYING OUT THE INVENTION

Hereinbelow, the present invention will be described in more detail with reference to the following Examples and Comparative Examples, but they should not be construed as limiting the scope of the present invention.

In the following Examples and Comparative Examples, the metal concentration of the metal-containing catalyst was measured by means of an ICP (inductively coupled plasma emission spectral analyzer) (JY38PII: manufactured and sold by Seiko Electronics Co., Ltd., Japan); the determination of the composition of the reaction mixture and the measurement of the respective concentrations of the components (such as an aromatic polyhydroxy compound, and a residue thereof bonded to carbonyl-containing groups originating from aromatic polycarbonates as the starting material, the reactant and the desired product; an aromatic monohydroxy compound; an aromatic carbonate; and anisole) in the reaction mixture were conducted by high performance liquid chromatography; and the measurement of the concentration of the aromatic polyhydroxy compound residue bonded to the catalyst in the reaction mixture was conducted by a method in which a ligand exchange with trifluoroacetic acid is conducted, followed by analysis by high performance liquid chromatography.

All of the concentrations are indicated by weight percentages.

EXAMPLE 1

(Preparation of catalyst)

A mixture of 30 kg of phenol, 10 kg of methyl phenyl carbonate and 8 kg of dibutyltin oxide was heated to and maintained at 180° C. for 10 hours, thereby performing a reaction. After that period of time, water formed in the resultant reaction mixture was distilled off together with unreacted phenol. Then, most of the remaining phenol and the remaining methyl phenyl carbonate were distilled off from the reaction mixture under reduced pressure, and the resultant mixture was allowed to cool under nitrogen atmosphere, to thereby obtain catalyst A.

(Production of aromatic carbonate)

The production of an aromatic carbonate was conducted using an apparatus shown in FIG. 2, which comprises distillation column 24 having a height of 1 m and a diameter of 4 inches and containing Dixon packing (6 mm φ), and a reaction vessel 100 having a capacity of 200 liters and equipped with a stirrer.

A mixture of dimethyl carbonate, phenol [concentration of 4,4'-dihydroxy diphenyl (i.e., an aromatic polyhydroxy compound) in phenol: 100 ppm] and catalyst A was continuously fed in liquid form from conduit 3 to reaction vessel 100 at a rate of 20 kg/hr, thereby performing a reaction. The weight ratio of the dimethyl carbonate to the phenol in the mixture was 50/50, and catalyst A was used in an amount such that the Sn concentration of the reaction mixture in conduit 13 became 0.4% by weight, wherein the Sn concentration can be confirmed using a sample withdrawn through a sampling nozzle (not shown) provided on conduit 13. The reaction conditions of the above reaction were such that the temperature in reaction vessel 100 was 200° C. and the pressure at the top of distillation column 24 was 6.2 kg/cm$^2$-G. Gas (containing methanol and dimethyl carbonate) formed in reaction vessel 100 was led into distillation column 24 through conduit 30. From distillation column 24, dimethyl carbonate was recycled to reaction vessel 100 through conduit 32, while the gas (containing methanol and dimethyl carbonate) distilled from the top of distillation column 24 was led into condenser 26 through conduit 25, in which the gas was condensed. A portion of the resultant condensate was recycled into distillation column 24 at a reflux ratio of 50 through conduits 27 and 28, and the rest of the condensate was continuously withdrawn at a rate of 2.3 kg/hr through conduit 29. A reaction mixture [containing methyl phenyl carbonate (as a desired reaction product), the catalyst, and an aromatic polyhydroxy compound and a residue thereof] was continuously withdrawn from the bottom of reaction vessel 100 at a rate of 17.7 kg/hr and led into evaporator 14 through conduit 13, from which an evaporated gas containing the methyl phenyl carbonate was withdrawn and led through conduit 21 into condenser 22, in which the evaporated gas was condensed. The resultant condensate was withdrawn from condenser 22 through conduit 23 at a rate of 16.67 kg/hr. On the other hand, an evaporation-concentrated liquid containing the catalyst and the aromatic polyhydroxy compound and the residue thereof was formed in evaporator 14. A portion of the concentrated liquid was led into reboiler 17 through conduits 15 and 16 and recycled into evaporator 14 through conduit 18. The rest of the concentrated liquid in evaporator 14 was recycled into reaction vessel 100 at a rate of 1 kg/hr through conduits 15, 19 and 3. During the period of time of from 300 hours to 2,000 hours after the start of the operation, a portion of the concentrated liquid formed in evaporator 14 was continuously withdrawn through conduit 20 at a rate of 0.03 kg/hr. Instead, catalyst A was added to reaction vessel 100 through conduit 3 in such an amount as to compensate for the amount of the catalyst withdrawn from conduit 20, so that the above-mentioned Sn concentration of 0.4% by weight was able to be maintained in conduit 13. The operation was conducted for 2,000 hours. During this period of time, the operation could be stably conducted (for example, both the flow and the composition in each conduit were stable) without suffering disadvantageous phenomena, such as the deposition of the catalyst from the catalyst-containing liquid-phase mixture and the adhesion of the deposited catalyst to the inner wall of the reaction vessel and the like. Samples were taken from the reaction mixture withdrawn from reaction vessel 100 through the above-mentioned sampling nozzle provided on conduit 13, which samples were, respectively, withdrawn at points in time of 500 hours, 1,000 hours, 1,500 hours and 2,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,000 hours, 1,500 hours and 2,000 hours after the start of the operation, the weight ratios (WRs) of the aromatic group-containing substance to Sn were, respectively, 0.19, 0.19, 0.2 and 0.2. The composition of the reaction mixture withdrawn from reaction vessel 100 through the above-mentioned sampling nozzle at the point in time of 2,000 hours after the start of the operation was as follows: phenol (PhOH): 51% by weight; methyl phenyl carbonate (MPC): 6% by weight; diphenyl carbonate (DPC): 0.4% by weight; anisole (ANS): 0.6% by weight; and Sn: 0.4% by weight. After the operation was stopped, the conditions of various parts of the apparatus were examined. As a result, no adhesion of the catalyst to the inner wall of each of reaction vessel 100, evaporator 14, reboiler 17 and conduits was observed.

Comparative Example 1

The production of an aromatic carbonate was conducted in substantially the same manner as in Example 1 except that the withdrawal of the evaporation-concentrated liquid formed in evaporator 14 (containing the catalyst and the aromatic polyhydroxy compound and the residue thereof) through conduit 20 was not conducted. Samples were taken from the reaction mixture withdrawn from reaction vessel 100 through the above-mentioned sampling nozzle provided on conduit 13, which samples were, respectively, withdrawn at points in time of 500 hours, 1,000 hours, 1,500 hours and 2,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,000 hours, 1,500 hours and 2,000 hours after the start of the operation, the weight ratios (WRs) of the aromatic group-containing substance to Sn were, respectively, 0.4, 1.0, 1.5 and 2.1. The composition of the reaction mixture withdrawn from reaction vessel 100 through the above-mentioned sampling nozzle at the point in time of 2,000 hours after the start of the operation was as follows: PhOH: 53% by weight; MPC: 3.5% by weight; DPC: 0.1% by weight; ANS: 0.5% by weight; and Sn: 0.3% by weight. After the operation was stopped, the conditions of various parts of the apparatus were examined. As a result, the adhesion of the catalyst to a part of the inner wall of each of reaction vessel 100, evaporator 14, reboiler 17 and conduits was observed.

Comparative Example 2

The production of an aromatic carbonate was conducted in substantially the same manner as in Example 1, except that phenol having a 4,4'-dihydroxy diphenyl concentration of 600 ppm by weight was used.

Samples were taken from the reaction mixture withdrawn from reaction vessel 100 through the above-mentioned sampling nozzle provided on conduit 13, which samples were, respectively, withdrawn at points in time of 500 hours, 1,000 hours, 1,500 hours and 2,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,000 hours, 1,500 hours and 2,000 hours after the start of the operation, the weight ratios (WRs) of the aromatic group-containing substance to Sn were, respectively, 0.9, 1.5, 2.0 and 2.6. The composition of the reaction mixture withdrawn from reaction vessel 100 through the above-mentioned sampling nozzle at the point in time of 2,000 hours after the start of the operation was as follows: PhOH: 53% by weight; MPC: 3.3% by weight; DPC: 0.1% by weight; ANS: 0.5% by weight; and Sn: 0.3% by weight. After the operation was stopped, the conditions of various parts of the apparatus were examined. As a result, the adhesion of the catalyst to a part of the inner wall of each of reaction vessel 100, evaporator 14 and conduits was observed.

EXAMPLE 2

(Preparation of catalyst)

A mixture of 40 kg of phenol and 8 kg of titanium tetrachloride was heated to and maintained at 50° C. for 10 hours, thereby performing a reaction. After that period of time, hydrogen chloride formed in the resultant reaction mixture was distilled off together with unreacted phenol. Then, most of the remaining phenol was distilled off from the reaction mixture under reduced pressure, and the resultant mixture was allowed to cool under nitrogen atmosphere, to thereby obtain catalyst B.

(Production of aromatic carbonate)

The production of aromatic carbonate was conducted in substantially the same manner as in Example 1 except that catalyst B was used in an amount such that the Ti concentration of the reaction mixture in conduit 13 became 0.2% by weight.

The operation was conducted for 2,000 hours. During this period of time, the operation could be stably conducted (for example, both the flow and the composition in each conduit were stable) without suffering disadvantageous phenomena, such as the deposition of the catalyst from the catalyst-containing liquid-phase mixture and the adhesion of the deposited catalyst to the inner wall of the reaction vessel and the like. Samples were taken from the reaction mixture withdrawn from reaction vessel 100 through the above-mentioned sampling nozzle provided on conduit 13, which samples were, respectively, withdrawn at points in time of 500 hours, 1,000 hours, 1,500 hours and 2,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,000 hours, 1,500 hours and 2,000 hours after the start of the operation, the weight ratios (WRs) of the aromatic group-containing substance to Ti were, respectively, 0.37, 0.38, 0.39 and 0.40. The composition of the reaction mixture withdrawn from reaction vessel 100 through the above-mentioned sampling nozzle at the point in time of 2,000 hours after the start of the operation was as follows: PhOH: 51% by weight; MPC: 6% by weight; DPC: 0.4% by weight; ANS: 0.4% by weight; and Ti: 0.2% by weight. After the operation was stopped, the conditions of various parts of the apparatus were examined. As a result, no adhesion of the catalyst to the inner wall of each of reaction vessel 100, evaporator 14, reboiler 17 and conduits was observed.

EXAMPLE 3

(Preparation of catalyst)

A mixture of 40 kg of phenol and 8 kg of lead monoxide was heated to and maintained at 180° C. for 10 hours, thereby performing a reaction. After that period of time, water formed in the resultant reaction mixture was distilled off together with unreacted phenol, to thereby obtain catalyst C.

(Production of aromatic carbonate)

The production of an aromatic carbonate was conducted using an apparatus shown in FIG. 1, which comprises continuous multi-stage distillation column 1 composed of a plate column having a height of 6 m and a diameter of 6 inches and equipped with 20 sieve trays.

A mixture of dimethyl carbonate, phenol [concentration of 4,4'-dihydroxy diphenyl (i.e., an aromatic polyhydroxy compound) in phenol: 150 ppm by weight] and catalyst C was continuously fed in liquid form from conduit 3 through preheater 4 and conduit 5 to continuous multi-stage distillation column 1 at a position of 0.5 m below top 2 thereof at a rate of 32 kg/hr, and was allowed to flow down inside multi-stage distillation column 1, thereby performing a reaction. The weight ratio of the dimethyl carbonate to the phenol in the mixture was 62/38, and catalyst C was used in an amount such that the Pb concentration of the reaction mixture in conduit 13 became 0.1% by weight, wherein the Pb concentration can be confirmed using a sample withdrawn through a sampling nozzle (not shown) provided on conduit 13. Dimethyl carbonate was fed from conduit 7 to evaporator 8 thereby forming a gas and the formed gas was fed from conduit 9 to bottom 6 of continuous multi-stage distillation column 1 at a rate of 26 kg/hr. The reaction conditions of the above reaction were such that the temperature at the bottom of continuous multi-stage distillation column 1 was 203° C. and the pressure at the top of continuous multi-stage distillation column 1 was 6.5 kg/cm$^2$-G. Gas distilled from top 2 was led into condenser 11 through conduit 10, in which the gas was condensed. The resultant condensate was continuously withdrawn at a rate of 25 kg/hr through conduit 12. A reaction mixture, containing methyl phenyl carbonate (as a desired reaction product), the catalyst, and an aromatic polyhydroxy compound and a residue thereof, was continuously withdrawn from bottom 6 at a rate of 34 kg/hr and led into evaporator 14 through conduit 13, from which an evaporated gas containing the methyl phenyl carbonate was withdrawn and led through conduit 21 into condenser 22, in which the gas was condensed. The resultant condensate was withdrawn from condenser 22 through conduit 23 at a rate of 32.95 kg/hr. On the other hand, an evaporation-concentrated liquid containing the catalyst and the aromatic polyhydroxy compound and the residue thereof was formed in evaporator 14. A portion of the concentrated liquid was led into reboiler 17 through conduits 15 and 16 and recycled into evaporator 14 through conduit 18. The rest of the concentrated liquid in evaporator 14 was recycled into continuous multi-stage distillation column 1 at a rate of 1 kg/hr through conduits 15, 19 and 3. During the period of time of from 400 hours to 3,000 hours after the start of the operation, a portion of the concentrated liquid formed in evaporator 14 was continuously withdrawn through conduit 20 at a rate of 0.05 kg/hr. Instead, catalyst C was added to continuous multi-stage distillation column 1 through conduit 3 in such an amount as to compensate for the amount of the catalyst withdrawn from conduit 20, so that the above-mentioned Pb concentration of 0.1 % by weight was able to be maintained in conduit 13. The operation was conducted for 3,000 hours. During this period of time, the operation could be stably conducted (for example, both the flow and the composition in each conduit were stable) without suffering disadvantageous phenomena, such as the deposition of the catalyst from the catalyst-containing liquid-phase mixture and the adhesion of the deposited catalyst to the inner wall of continuous multi-stage distillation column 1 and the like. Samples were taken from the reaction mixture withdrawn from continuous multi-stage distillation column 1 through the above-mentioned sampling nozzle provided on conduit 13, which samples were, respectively, withdrawn at points in time of 500 hours, 1,200 hours, 2,100 hours and 3,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,200 hours, 2,100 hours and 3,000 hours after the start of the operation, the weight ratios (WRs) of the aromatic group-containing substance to Pb were, respectively, 0.11, 0.11, 0.12 and 0.12. The composition of the reaction mixture withdrawn from continuous multi-stage distillation column 1 through the above-mentioned sampling nozzle provided on conduit 13 at the point in time of 3,000 hours after the start of the operation was as follows: PhOH: 31% by weight; MPC: 9% by weight; DPC: 0.5% by weight; ANS: 0.1% by weight; and Pb: 0.1% by weight. After the operation was stopped, the conditions of various parts of the apparatus were examined. As a result, no adhesion of the catalyst to the inner wall of each of continuous multi-stage distillation column 1, evaporator 14, reboiler 17 and conduits was observed.

Comparative Example 3

The production of an aromatic carbonate was conducted in substantially the same manner as in Example 3, except that the withdrawal of the evaporation-concentrated liquid formed in evaporator 14 (containing the catalyst and the aromatic polyhydroxy compound and the residue thereof) through conduit 20 was not conducted. Samples were taken from the reaction mixture withdrawn from continuous multi-stage distillation column 1 through the above-mentioned sampling nozzle provided on conduit 13, which samples were, respectively, withdrawn at points in time of 500 hours, 1,200 hours, 2,100 hours and 3,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,200 hours, 2,100 hours and 3,000 hours after the start of the operation, the weight ratios (WRs) of the aromatic group-containing substance to Pb were, respectively, 0.2, 0,7, 1.4 and 2.1. The composition of the reaction mixture withdrawn from continuous multi-stage distillation column 1 through the above-mentioned sampling nozzle at the point in time of 3,000 hours after the start of the operation was as follows: PhOH: 33% by weight; MPC: 6.5% by weight; DPC: 0.2% by weight; ANS: 0.1% by weight; and Pb: 0.1% by weight. After the operation was stopped, the conditions of various parts of the apparatus were examined. As a result, the adhesion of the catalyst to a part of the inner wall of each of continuous multi-stage distillation column 1, evaporator 14 and conduits was observed.

Comparative Example 4

The production of an aromatic carbonate was conducted in substantially the same manner as in Example 3, except that a by-produced phenol formed during the transesterification of diphenyl carbonate with bisphenol A to produce a polycarbonate was used. The phenol contained 15% by weight of diphenyl carbonate and 500 ppm by weight of bisphenol A.

Samples were taken from the reaction mixture withdrawn from continuous multi-stage distillation column 1 through the above-mentioned sampling nozzle provided on conduit 13, which samples were, respectively, withdrawn at points in time of 500 hours, 1,200 hours, 2,100 hours and 3,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,200 hours, 2,100 hours and 3,000 hours after the start of the operation, the weight ratios (WRs) of the aromatic group-containing substance to Pb were, respectively, 0.7, 1.7, 2.6 and 4.0. The composition of the reaction mixture withdrawn from continuous multi-stage distillation column 1 through the above-mentioned sampling nozzle at the point in time of 3,000 hours after the start of the operation was as follows: PhOH: 34% by weight; MPC: 5.8% by weight; DPC: 0.2% by weight; ANS: 0.1% by weight; and Pb: 0.1% by weight. After the operation was stopped, the conditions of various parts of the apparatus were examined. As a result, the adhesion of the catalyst to a part of the inner wall of each of continuous multi-stage distillation column 1, evaporator 14 and conduits was observed.

EXAMPLE 4

Figure 3:
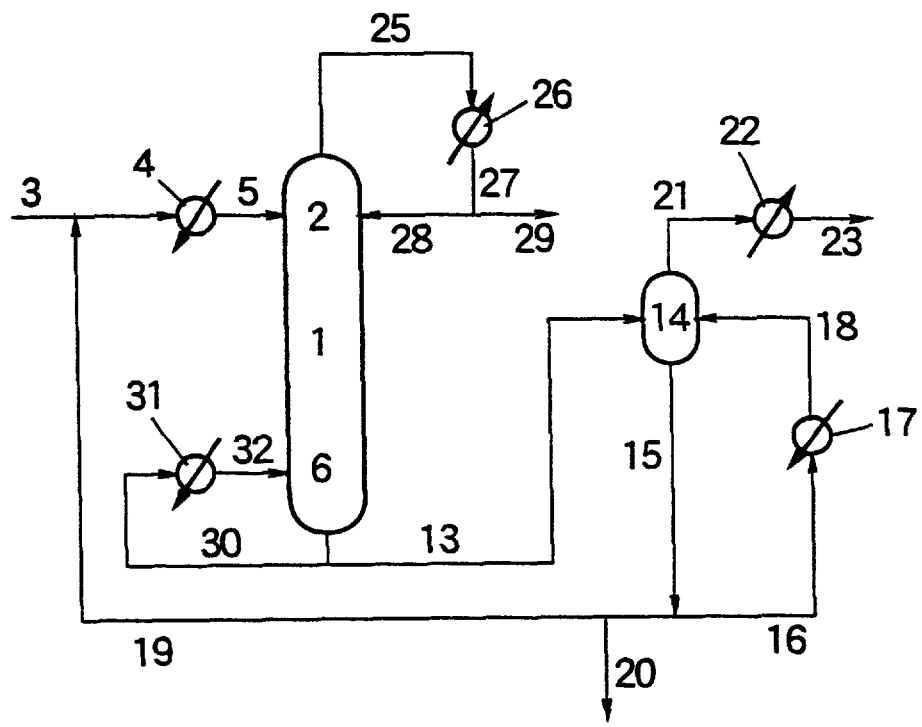
FIG. 3 is a diagram showing a further example of systems for practicing the process of the present invention.

The production of diphenyl carbonate from methyl phenyl carbonate was conducted using catalyst C obtained in Example 3, and an apparatus shown in FIG. 3, which comprises continuous multi-stage distillation column 1 comprised of a plate column which has a height of 6 m and a diameter of 4 inch, and is equipped with 20 sieve trays.

A mixture of methyl phenyl carbonate and catalyst C was continuously fed in liquid form from conduit 3 through preheater 4 and conduit 5 to continuous multistage distillation column 1 at a position of 2.0 m below top 2 thereof at a rate of 10 kg/hr, and was allowed to flow down inside multi-stage distillation column 1, thereby performing a reaction. Catalyst C was used in an amount such that the Pb concentration of the reaction mixture in conduit 13 became 0.1% by weight, wherein the Pb concentration can be confirmed using a sample withdrawn through a sampling nozzle (not shown) provided on conduit 13. The reaction conditions of the above reaction were such that the temperature at the bottom of continuous multi-stage distillation column 1 was 195° C. and the pressure at the top of continuous multi-stage distillation column 1 was 194 mmHg. Gas distilled from top 2 was led into condenser 26 through conduit 25, in which the gas was condensed. A portion of the resultant condensate was recycled into top 2 through conduits 27 and 28, and the rest of the condensate was continuously withdrawn at a rate of 2.4 kg/hr through conduits 27 and 29. A portion of the reaction mixture containing diphenyl carbonate (as a desired reaction product), the catalyst, and an aromatic polyhydroxy compound and a residue thereof, was withdrawn from bottom 6 of continuous multi-stage distillation column 1 and recycled to bottom 6 through conduit 30, reboiler 31 and conduit 32. The rest of the reaction mixture was continuously withdrawn from bottom 6 at a rate of 7.6 kg/hr and led into evaporator 14 through conduit 13, from which an evaporated gas containing the diphenyl carbonate was withdrawn and led through conduit 21 into condenser 22, in which the gas was condensed. The resultant condensate was withdrawn from condenser 22 through conduit 23 at a rate of 5.55 kg/hr. On the other hand, an evaporation-concentrated liquid containing the catalyst and the aromatic polyhydroxy compound and the residue thereof was formed in evaporator 14. A portion of the concentrated liquid was led into reboiler 17 through conduits 15 and 16 and recycled into evaporator 14 through conduit 18. The rest of the concentrated liquid in evaporator 14 was recycled into continuous multi-stage distillation column 1 at a rate of 2 kg/hr through conduits 15, 19 and 3. During the period of time of from 400 hours to 3,000 hours after the start of the operation, a portion of the concentrated liquid formed in evaporator 14 was continuously withdrawn through conduit 20 at a rate of 0.05 kg/hr. Instead, catalyst C was added to continuous multi-stage distillation column 1 through conduit 3 in such an amount as to compensate for the amount of the catalyst withdrawn from conduit 20, so that the above-mentioned Pb concentration of 0.1% by weight was able to be maintained in conduit 13. The operation was conducted for 3,000 hours. During this period of time, the operation could be stably conducted (for example, both the flow and the composition in each conduit were stable) without suffering disadvantageous phenomena, such as the deposition of the catalyst from the catalyst-containing liquid-phase mixture and the adhesion of the deposited catalyst to the inner wall of continuous multi-stage distillation column 1 and the like. Samples were taken from the reaction mixture withdrawn from continuous multi-stage distillation column 1 through the above-mentioned sampling nozzle provided on conduit 13, which samples were, respectively, withdrawn at points in time of 500 hours, 1,200 hours, 2,100 hours and 3,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples respectively withdrawn at points in time of 500 hours, 1,200 hours, 2,100 hours and 3,000 hours after the start of the operation, the weight ratios (WRs) of the aromatic group-containing substance to Pb were, respectively, 0.20, 0.21, 0.21 and 0.21. The composition of the reaction mixture withdrawn from continuous multi-stage distillation column 1 through the above-mentioned sampling nozzle provided on conduit 13 at the point in time of 3,000 hours after the start of the operation was as follows: MPC: 24.1% by weight; DPC: 75.6% by weight; and Pb: 0.1% by weight. After the operation was stopped, the conditions of various parts of the apparatus were examined. As a result, no adhesion of the catalyst to the inner wall of each of continuous multi-stage distillation column 1, evaporator 14, reboiler 17 and conduits was observed.

EXAMPLE 5

Figure 4:
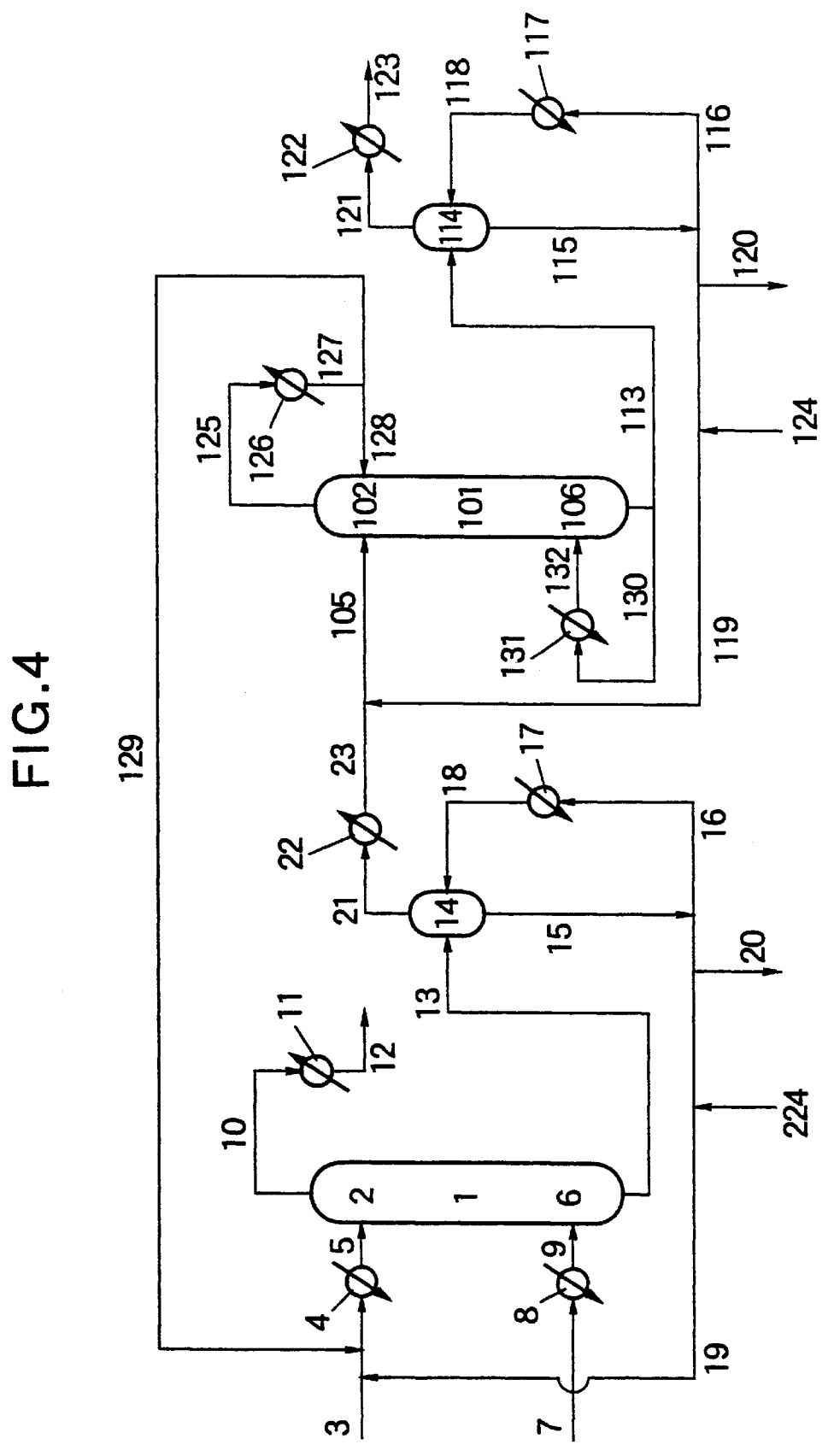

The production of diphenyl carbonate was conducted using catalyst C prepared in Example 3, and the apparatus shown in FIG. 4.

A mixture of dimethyl carbonate, phenol (the concentration of 4-,4'-dihydroxyphenyl as an aromatic polyhydroxy compound in the phenol: 200 ppm by weight) and methyl phenyl carbonate was fed in liquid form to continuous multi-stage distillation column 1 at a position 0.5 m below the top 2 thereof (which column was comprised of a plate column having a height of 12 m and a diameter of 8 inches, and provided with 40 sieve trays) at a rate of 31 kg/hr from conduit 3 through preheater 4 and conduit 5, thereby allowing the mixture to flow down inside continuous multi-stage distillation column 1 so as to perform a reaction. The composition of the mixture fed from conduit 3 was controlled so that the mixture flowing through conduit 5 during the operation (the mixture flowing through conduit 5 was comprised of a liquid introduced from conduit 19, which was recycled from evaporator 14; a liquid introduced from conduit 129, which was recycled from continuous multi-stage distillation column 101; and the above-mentioned mixture fed from conduit 3) had a composition of 49.9% by weight of dimethyl carbonate, 44.7% by weight of phenol and 4.9% by weight of methyl phenyl carbonate. Dimethyl carbonate was fed through conduit 7 to evaporator 8, in which the dimethyl carbonate was subjected to evaporation. The resultant gas was fed to bottom 6 of continuous multi-stage distillation column 1 through conduit 9 at a rate of 55 kg/hr. Catalyst C was fed from conduit 224 in such an amount that the Pb concentration at conduit 13 became 0.2% by weight, wherein the Pb concentration can be confirmed using the reaction mixture withdrawn from a sampling nozzle (not shown) provided on conduit 13. Continuous multi-stage distillation column 1 was operated under conditions such that the temperature at the column bottom was 203° C. and the pressure at the column top was 6.5 kg/cm$^2$-G. Continuous multi-stage distillation column 1 was clothed with a heat insulating material and a part of the column was heated by a heater (not shown). Gas distilled from top 2 of the column was led through conduit 10 to condenser 11, in which the gas was condensed. The resultant condensate was continuously withdrawn at a rate of 55 kg/hr from conduit 12. A reaction mixture was withdrawn continuously from bottom 6 at a rate of 31 kg/hr, and was led to evaporator 14 through conduit 13. In evaporator 14, an evaporation-concentrated liquid containing the catalyst and the aromatic polyhydroxy compound and residue thereof was formed. A portion of the concentrated liquid was recycled to evaporator 14 through conduits 15 and 16, reboiler 17 and conduit 18. The rest of the concentrated liquid was recycled into continuous multi-stage distillation column 1 at a rate of 1 kg/hr through conduits 15, 19 and 3. During the period of time from 400 hours to 3000 hours after the start of the operation, a portion of the concentrated liquid formed in evaporator 14 was continuously withdrawn from conduit 20 at a rate of 0.05 kg/hr. Instead, catalyst C was fed from conduit 224 in such an amount as to compensate for the amount of the catalyst withdrawn from conduit 20, so that the above-mentioned Pb concentration of 0.2% by weight was able to be maintained in conduit 13. On the other hand, an evaporated gas formed in evaporator 14 was led into condenser 22 through conduit 21, in which the gas was condensed. The resultant condensate was fed to continuous multistage distillation column 101 at a position of 2.0 m below top 102 thereof through conduits 23 and 105, which column was comprised of a plate column having a height of 6 m and a diameter of 10 inches, and provided with 20 sieve trays, thereby performing a reaction. The composition of the mixture in conduit 105 was as follows: dimethyl carbonate: 43.1% by weight; phenol: 24.5% by weight; methyl phenyl carbonate: 27.1% by weight; and diphenyl carbonate: 4.5% by weight (the mixture at conduit 105 was comprised of a liquid introduced from conduit 23 and a liquid introduced from conduit 119, which was recycled from evaporator 114). Catalyst C was fed from conduit 124 in an amount such that the Pb concentration at conduit 113 became 0.2% by weight, wherein the Pb concentration can be confirmed using a sample withdrawn from a sampling nozzle (not shown) provided on conduit 113. Continuous multistage distillation column 101 was operated under conditions such that the temperature at the column bottom was 198° C. and the pressure at the column top was 280 mmHg. Gas distilled from column top 102 was led through conduit 125 to condenser 126, in which the gas was condensed. A portion of the resultant condensate was recycled into column top 102 through conduit 128, and the rest of the condensate was recycled into continuous multi-stage distillation column 1 through conduits 127 and 129, preheater 4 and conduit 5. After the start of the recycling of the condensate into continuous multi-stage distillation column 1 through conduit 129, phenol (having a concentration of 4,4'-dihydroxydiphenyl as an aromatic polyhydroxy compound of 200 ppm by weight) was added to the mixture fed from conduit 3 in an amount such that the above-mentioned composition of the mixture at conduit 5 can be maintained. A portion of the reaction mixture at bottom 106 of continuous multi-stage distillation column 101 was led into reboiler 131 through conduit 130, and recycled into column bottom 106 through conduit 132, and the rest of the reaction mixture was led to evaporator 114 through conduit 113 at a rate of 6.9 kg/hr. In evaporator 114, an evaporation-concentrated liquid containing the catalyst and the aromatic polyhydroxy compound and the residue thereof was formed. A portion of the concentrated liquid was led into reboiler 117 through conduits 115 and 116 and recycled into evaporator 114 through conduit 118. The rest of the concentrated liquid in evaporator 114 was recycled into continuous multi-stage distillation column 101 through conduits 115, 119 and 105 at a rate of 2 kg/hr. During the period of time of from 400 hours to 3,000 hours after the start of the operation, a portion of the concentrated liquid formed in evaporator 114 was continuously withdrawn through conduit 120 at a rate of 0.1 kg/hr. Instead, catalyst C was fed from conduit 124 in such an amount as to compensate for the amount of the catalyst withdrawn from conduit 120, so that the above-mentioned Pb concentration of 0.2% by weight can be maintained in conduit 113. On the other hand, an evaporated gas formed in evaporator 114 was led to condenser 122 through conduit 121 and withdrawn through conduit 123 at a rate of 6.8 kg/hr. The liquid-phase mixture withdrawn from conduit 123 had a diphenyl carbonate content of 98% by weight. The operation was conducted for 3,000 hours. During this period of time, the operation could be stably conducted (for example, both the flow and the composition in each conduit were stable) without suffering disadvantageous phenomena, such as the clogging of a conduit, which is liable to be caused by the deposition of the catalyst from the catalyst-containing liquid-phase mixture and the adhesion of catalyst to the inner wall of the conduit. Samples were taken from the reaction mixtures withdrawn from continuous multi-stage distillation columns 1 and 101, respectively, through the sampling nozzle provided on conduit 13 and the sampling nozzle provided on conduit 113, which samples were withdrawn at points in time of 500 hours, 1,200 hours, 2,100 hours and 3,000 hours after the start of the operation. The determination of the concentrations of dihydroxy diphenyl, dihydroxy benzophenone, and residues thereof as aromatic group-containing substances (i.e., an aromatic polyhydroxy compound and a residue thereof) in each sample was conducted by the above-mentioned method. With respect to the samples withdrawn through conduit 13, respectively, at points in time of 500 hours, 1,200 hours, 2,100 hours and 3,000 hours after the start of the operation, the weight ratios (WRs) of the aromatic group-containing substance to Pb were, respectively, 0.40, 0.41, 0.42 and 0.42. With respect to the samples withdrawn through conduit 113, respectively, at points in time of 500 hours, 1,200 hours, 2,100 hours and 3,000 hours after the start of the operation, the weight ratios (WRs) of the aromatic group-containing substance to Pb were, respectively, 0.16, 0.17, 0.17 and 0.18. After the operation was stopped, the conditions of various parts of the apparatus were examined. As a result, no adhesion of the catalyst to the inner wall of each of continuous multi-stage distillation column 1, evaporator 14, reboiler 17, and conduits was observed.

INDUSTRIAL APPLICABILITY

According to the present invention, in a process for producing an aromatic carbonate by transesterification of a starting material with a reactant in the presence of a metal-containing catalyst, the transesterification is conducted while maintaining a weight ratio (WR) of at least one aromatic group-containing substance selected from the group consisting of a specific aromatic polyhydroxy compound and a residue thereof to the metal of the metal-containing catalyst at 2.0 or less, wherein the weight ratio (WR) is measured with respect to a catalyst-containing liquid-phase mixture in a system for the transesterification, and wherein the aromatic group-containing substance originates from the starting material, the reactant and/or a by-product of the transesterification. By the process of the present invention, the transesterification reaction can be conducted without suffering disadvantageous phenomena, such as the deposition of the catalyst from the catalyst-containing liquid-phase mixture and the adhesion of the deposited catalyst to the inner walls of the reactor, pipes and the like, so that the desired aromatic carbonate can be produced stably for a prolonged period of time.

In conducting a transesterification reaction for producing an aromatic carbonate, which is important, for example, as a raw material for producing an aromatic polycarbonate, the process of the present invention can be advantageously used either when the reaction is performed in a batchwise manner or when the reaction is performed in a continuous manner. According to the present invention, especially when the production of an aromatic carbonate is conducted in a continuous manner, the continuous production of an aromatic carbonate can be conducted extremely efficiently for a prolonged period of time by withdrawing a part of the catalyst-containing liquid-phase mixture out of a system for the transesterification.

We claim:

1. In a process for producing an aromatic carbonate which comprises transesterifying, in the presence of a metal-containing catalyst, a starting material selected from the group consisting of a dialkyl carbonate represented by the following formula (1):

$$R^1OCOR^1, \quad (1)$$

an alkyl aryl carbonate represented by the following formula (2):

$$R^2OCOAr^2 \quad (2)$$

and a mixture thereof with a reactant selected from the group consisting of an aromatic monohydroxy compound represented by the following formula (3):

$$Ar^1OH \quad (3),$$

an alkyl aryl carbonate represented by the following formula (4):

$$R^3OCOAr^3 \quad (4)$$

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms and each of $Ar^1$, $Ar^2$ and $Ar^3$ independently represents an aromatic group having 5 to 30 carbon atoms, to thereby produce at least one aromatic carbonate selected from the group consisting of an alkyl aryl carbonate and a diaryl carbonate, which is selected in correspondence to the starting material and the reactant and represented by at least one formula selected from the group consisting of the following formulae (5) and (6):

$$ROCOAr \quad \text{and} \quad (5)$$

$$ArOCOAr, \quad (6)$$

wherein R and Ar are, respectively, selected from $R^1$, $R^2$ and $R^3$ and selected from $Ar^1$, $Ar^2$ and $Ar^3$ in correspondence to the starting material and the reactant, the improvement in which said transesterification is conducted while maintaining a weight ratio (WR) of at least one aromatic group-containing substance selected from the group consisting of an aromatic polyhydroxy compound and a residue thereof to the metal of said metal-containing catalyst at 2.0 or less, wherein said weight ratio (WR) is measured with respect to a catalyst-containing liquid-phase mixture in a system for said transesterification, and wherein said aromatic group-containing substance originates from at least one member selected from the group consisting of said starting material, said reactant and a by-product of said transesterification, said aromatic polyhydroxy compound being represented by the following formula (7):

wherein $Ar^4$ represents an aromatic group having a valence of m, m represents an integer of 2 or more, and each —OH group is individually bonded to an arbitrary ring-carbon position of the $Ar^4$ group, and said residue of the aromatic polyhydroxy compound being represented by the following formula (8):

wherein $Ar^4$ and m are as defined above, n represents an integer of from 1 to m, and each of the —OH group and the —O— group is individually bonded to an arbitrary ring-carbon position of the $Ar^4$ group, and being present in such a form as chemically bonded to at least one member selected from the group consisting of the metal of said catalyst, an alkoxycarbonyl group derived from said dialkyl carbonate or said alkyl aryl carbonate, an aryloxycarbonyl group derived from said alkyl aryl carbonate or said diaryl carbonate, and a carbonyl group derived from said dialkyl carbonate, said alkyl aryl carbonate or said diaryl carbonate.

2. The process according to claim 1, wherein said aromatic polyhydroxy compound is at least one member selected from the group consisting of:

(A) an oxidation product of an aromatic monohydroxy compound as said reactant, (B) at least one member selected from the group consisting of a product produced by the Fries rearrangement of a diaryl carbonate obtained by said transesterification and an oxidation product of said product and (C) at least one member selected from the group consisting of aromatic dihydroxy compounds derived from phenol as the reactant and represented by the following formula (9):

wherein $Y^1$ represents a single bond, a divalent alkane group having 1 to 30 carbon atoms or a divalent group selected from —O—, —Co—, —S—, —SO$_2$, —SO— and —COO—, and oxidation products of said aromatic dihydroxy compounds.

3. The process according to claim 1 or 2, wherein the maintenance of said weight ratio (WR) at 2.0 or less is performed by using as the reactant an aromatic monohydroxy compound containing said aromatic polyhydroxy compound in a controlled concentration, and withdrawing a part of said catalyst-containing liquid-phase mixture out of said system for the transesterification.

4. The process according to claim 3, wherein said aromatic monohydroxy compound has an aromatic polyhydroxy compound concentration of 400 ppm by weight or less.

5. The process according to claim 1, which is for continuously producing said at least one aromatic carbonate, wherein a transesterification reaction mixture containing said at least one aromatic carbonate and containing said catalyst is continuously withdrawn from a reactor for said transesterification.

6. The process according to claim 5, wherein said aromatic monohydroxy compound as the reactant comprises a mixture of a feedstock aromatic monohydroxy compound and an unreacted aromatic monohydroxy compound recycled from said reactor, wherein said feedstock aromatic monohydroxy compound has an aromatic polyhydroxy compound concentration of 400 ppm by weight or less.

7. The process according to claim 5 or 6, wherein a part of said reaction mixture, containing said catalyst, withdrawn from said reactor is subjected to evaporation, and the resultant mixture having an increased catalyst concentration is at least partly withdrawn out of said system for the transesterification to thereby maintain said weight ratio (WR) at 2.0 or less.

8. The process according to claim 5 or 6, wherein said starting material and said reactant are continuously fed to a continuous multi-stage distillation column to effect a transesterification reaction therebetween in at least one phase selected from a liquid phase and a gas-liquid phase in the presence of the metal-containing catalyst in said distillation column, while continuously withdrawing a high boiling point reaction mixture containing said at least one aromatic carbonate in a liquid form from a lower portion of the distillation column and continuously withdrawing a low boiling point reaction mixture containing a by-product in a gaseous form from an upper portion of the distillation column by distillation.

9. The process according to claim 7, wherein said starting material and said reactant are continuously fed to a continuous multi-stage distillation column to effect a transesterification reaction therebetween in at least one phase selected from a liquid phase and a gas-liquid phase in the presence of the metal-containing catalyst in said distillation column, while continuously withdrawing a high boiling point reaction mixture containing said at least one aromatic carbonate in a liquid form from a lower portion of the distillation column and continuously withdrawing a low boiling point reaction mixture containing a by-product in a gaseous form from an upper portion of the distillation column by distillation.

* * * * *